(12) United States Patent
Nishino et al.

(10) Patent No.: US 8,729,484 B2
(45) Date of Patent: May 20, 2014

(54) RADIOGRAPHIC IMAGING DEVICE AND RADIOGRAPHIC IMAGING SYSTEM

(75) Inventors: Naoyuki Nishino, Kanagawa (JP); Haruyasu Nakatsugawa, Kanagawa (JP); Naoto Iwakiri, Kanagawa (JP); Yasunori Ohta, Kanagawa (JP); Fumito Nariyuki, Kanagawa (JP); Kazuhiro Noda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 123 days.

(21) Appl. No.: 13/281,443

(22) Filed: Oct. 26, 2011

(65) Prior Publication Data

US 2012/0119097 A1 May 17, 2012

(30) Foreign Application Priority Data

Nov. 15, 2010 (JP) ................................. 2010-254886

(51) Int. Cl.
*G01T 1/24* (2006.01)
(52) U.S. Cl.
CPC ..................................... *G01T 1/244* (2013.01)
USPC .................................................... 250/370.09
(58) Field of Classification Search
CPC .......... H01L 31/14; H01L 31/12; G01T 1/244
USPC .................................................... 250/370.09
See application file for complete search history.

(56) References Cited

U.S. PATENT DOCUMENTS

| | | | | |
|---|---|---|---|---|
| 6,359,965 | B1 * | 3/2002 | Finkler et al. | 378/98.3 |
| 7,426,259 | B2 * | 9/2008 | Weisfield | 378/98.8 |
| 7,791,035 | B2 * | 9/2010 | Yokoyama et al. | 250/370.09 |
| 2011/0024641 | A1 | 2/2011 | Yokoyama et al. | |

FOREIGN PATENT DOCUMENTS

| | | | |
|---|---|---|---|
| JP | 07261295 A | * | 10/1995 |
| JP | 2008-256675 A | | 10/2008 |
| JP | 2009011526 A | * | 1/2009 |
| WO | 2010/150381 | | 12/2010 |

OTHER PUBLICATIONS

Partial English language translation of the following: Office action dated Dec. 10, 2013 from the Japanese Patent Office in a Japanese patent application corresponding to the instant patent application. This office action translation is submitted now in order to supplement the understanding of patent document WO 2010/150381 which is cited in the office action and is being disclosed in the instant information Disclosure Statement.

* cited by examiner

*Primary Examiner* — Constantine Hannaher
(74) *Attorney, Agent, or Firm* — SOLARIS Intellectual Property Group, PLLC

(57) ABSTRACT

There is provided a radiographic imaging device including: an imaging panel at which sensor portions, that detect radiation or light converted from radiation, are formed at a detection region, and that captures a radiographic image expressed by radiation or light converted from radiation; a light illuminating section at which light-emitting portions, that can individually illuminate light for erasing residual images, are provided per sectional region obtained by dividing the detection region into the sectional regions; a storage section that stores imaging actual results information that expresses past actual results of imaging carried out by the imaging panel; and a control section that, in accordance with at least one of actual results of imaging and imaging conditions, controls absence/presence of illumination of, light amount of, and illumination time period of light from the respective light-emitting portions of the light illuminating section.

9 Claims, 21 Drawing Sheets

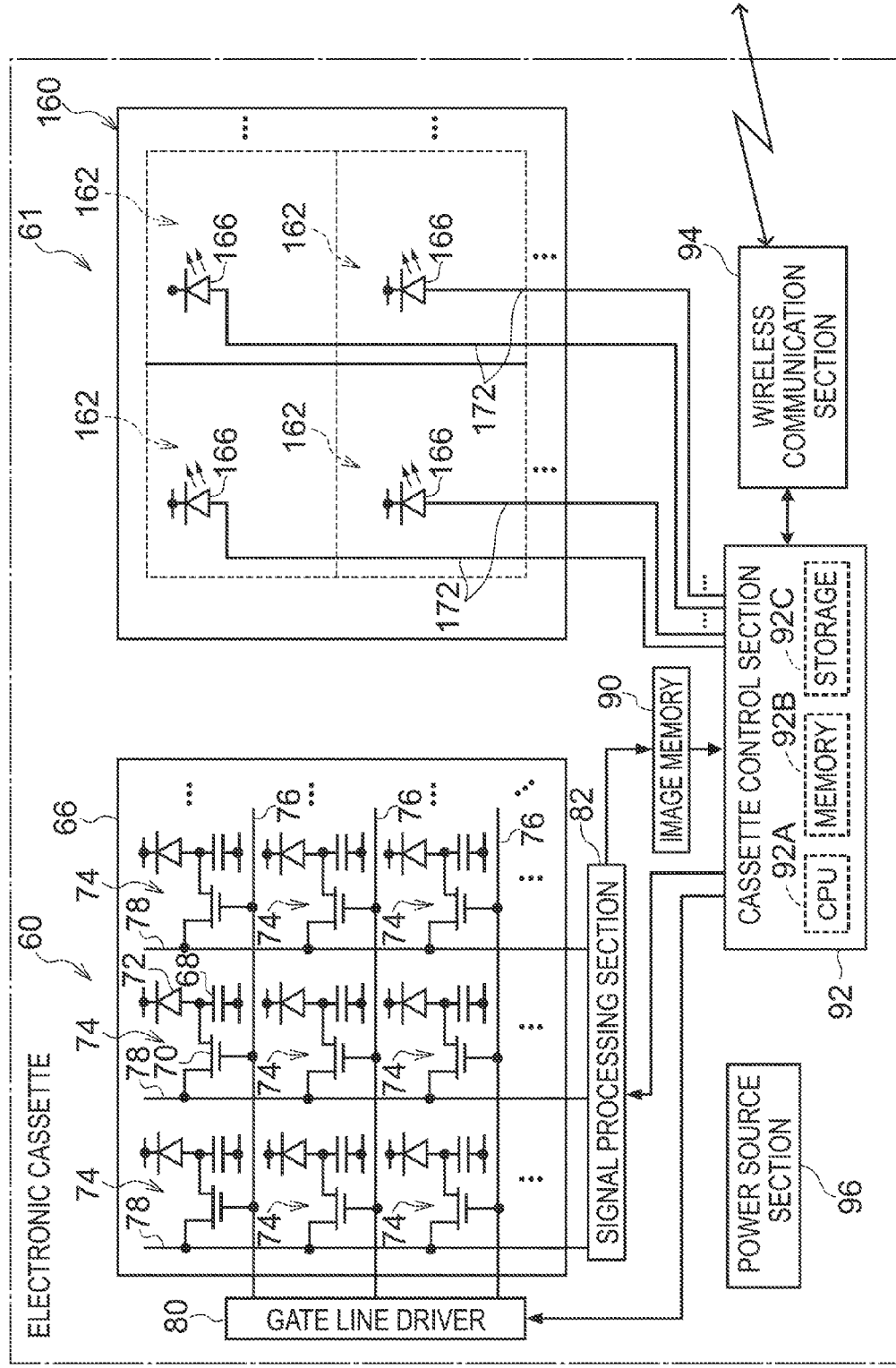

RADIOGRAPHIC IMAGING DEVICE AND RADIOGRAPHIC IMAGING SYSTEM

CROSS-REFERENCE TO RELATED APPLICATION

This application is based on and claims priority under 35 USC 119 from Japanese Patent Application No. 2010-254886 filed on Nov. 15, 2010, the disclosure of which is incorporated by reference herein.

BACKGROUND

1. Technical Field

The present invention relates to a radiographic imaging device and a radiographic imaging system, and in particular, relates to a radiographic imaging device and a radiographic imaging system that carry out capturing of a radiographic image expressed by radiation that is emitted from a radiation source and passes through a subject.

2. Related Art

Radiation detectors such as FPDs (Flat Panel Detectors), in which a radiation-sensitive layer is disposed on a TFT (Thin Film Transistor) active matrix substrate and that can convert radiation such as X-rays or the like directly into digital data, and the like have been put into practice in recent years. A radiographic imaging device, that captures radiographic images expressed by irradiated radiation, is put into practice by using this radiation detector. As compared with a radiographic imaging device that uses conventional X-ray films or imaging plates, a radiographic imaging device using this radiation detector has the advantages that an image can be confirmed immediately, and through-imaging (fluorscopic imaging), which is video imaging that carries out capturing of radiographic images continuously, can also be carried out.

Various types of such radiation detectors have been proposed. For example, there are: an indirect-conversion-type radiation detector that once converts radiation into light at a scintillator of CsI:Tl, GOS ($Gd_2O_2S$:Tb), or the like, and, at sensor portions such as photodiodes or the like, converts the converted light into charges, and accumulates the charges; a direct-conversion-type radiation detector that converts radiation into charges at a semiconductor layer of amorphous selenium or the like; and the like. In the radiographic imaging device, the charges accumulated in the radiation detector are read-out as electric signals, and, after the read-out electric signals are amplified at an amplifier, the amplified signals are converted into digital data at an A/D (analog/digital) converting section.

In an indirect-conversion-type or direct-conversion-type radiation detector, there are cases in which charges become trapped in impurity potentials within the sensor portions, such as photodiodes, or within the semiconductor layer, and residual images arise.

A light calibration method is known as a technique for erasing such residual images. In the light calibration method, noise is reduced by forming the substrate of a radiation detector of a material that is light-transmissive, placing a light guide plate on the substrate side, illuminating light from the substrate side, and filling-in the impurity potentials of the respective sensor portions of the radiation detector before imaging.

For example, Japanese Patent Application Laid-Open (JP-A) No. 2008-256675 discloses a technique in which plural light sources that can emit light are disposed with respect to one surface of a planar detector that includes a conversion section in which plural pixels, that include converting elements that can convert radiation into charges, are disposed in the form of a matrix. A signal that is acquired at a predetermined cycle from the planar detector and a reference value that is set in advance are compared. On the basis of the results of comparison, light is discharged from the plural light sources with respect to the entire one surface of the planar detector.

However, in the technique of JP-A No. 2008-256675, the occurrence of residual images can be suppressed, but because light is illuminated with respect to an entire one surface of the planar detector from the light sources, there is the problem that consumption of electric power cannot be suppressed.

In recent years, portable radiographic imaging devices (hereinafter also called "electronic cassettes") also have been put into practice. The electronic cassette incorporates therein a radiation detector, a control section including an image memory, and a power source section such as a battery or the like, and stores, in the image memory, radiographic image data that is outputted from the radiation detector. Because the electronic cassette is operated by electric power from the power source section such as a battery or the like, if the capacity of the battery is made to be large, the weight of the electronic cassette increases, the portability deteriorates, and further, the size of the device also is increased. Therefore, in electronic cassettes in particular, it is important to suppress consumption of electric power.

SUMMARY

The present invention was made in view of the above-described circumstances, and an object thereof is to provide a radiographic imaging device and a radiographic imaging system that suppress electric power consumption while suppressing the occurrence of residual images.

In order to achieve the above-described object, the first aspect of the present invention provides a radiographic imaging device including:

an imaging panel at which plural sensor portions, that detect radiation or light converted from radiation, are formed at a detection region, and that captures a radiographic image expressed by radiation or light converted from radiation;

a light illuminating section at which plural light-emitting portions, that can individually illuminate light for erasing residual images, are provided per sectional region obtained by dividing the detection region into plural the sectional regions;

a storage section that stores imaging actual results information that expresses past actual results of imaging carried out by the imaging panel; and a control section that, in accordance with at least one of actual results of imaging, that are expressed by the imaging actual results information stored in the storage section, and imaging conditions, controls absence/presence of illumination of, light amount of, and illumination time period of light from the respective light-emitting portions of the light illuminating section.

In accordance with the first aspect of the present invention, plural sensor portions, that detect radiation or light converted from radiation, are formed at the detection region of the imaging panel, and the imaging panel captures a radiographic image expressed by radiation or light converted from radiation. Further, at the light illuminating section, plural light-emitting portions, that can individually illuminate light for erasing residual images, are provided per sectional region obtained by dividing the detection region into plural sectional regions. Moreover, imaging actual results information, that expresses past actual results of imaging carried out by the imaging panel, is stored in the storage section.

The absence/presence of illumination of, the light amount of, and the illumination time period of light from the respective light-emitting portions of the light illuminating section are controlled by the control section in accordance with at least one of actual results of imaging, that are expressed by the imaging actual results information stored in the storage section, and imaging conditions.

In this way, in accordance with the first aspect of the present invention, the plural light-emitting portions, that can individually illuminate light for erasing residual images, are provided per sectional region obtained by dividing, into plural sectional regions, the detection region of the imaging panel at which the plural sensor portions, that detect radiation or light converted from radiation, are formed. The absence/presence of illumination of, the light amount of, and the illumination time period of light from the respective light-emitting portions are controlled in accordance with at least one of actual results of imaging and imaging conditions. Due thereto, consumption of electric power can be suppressed while the occurrence of residual images is suppressed.

The second aspect of the present invention provides the radiographic imaging device of the first aspect, wherein the imaging conditions comprise information that designates which of still imaging, that carries out imaging one at a time, and through imaging, that carries out imaging continuously, is to be carried out, and when through imaging is designated as the imaging condition, the control section causes light to be illuminated from the respective light-emitting portions of the light illuminating section synchronously with imaging.

The third aspect of the present invention provides the radiographic imaging device of the first aspect, wherein the imaging conditions comprise information designating a frame rate of through imaging, and when the frame rate of through imaging that is designated as the imaging condition is greater than or equal to a predetermined threshold value, the control section causes light to be illuminated from the respective light-emitting portions of the light illuminating section synchronously with imaging.

The fourth aspect of the present invention provides the radiographic imaging device of the first aspect, further including:

an acquisition section that acquires a position of an imaging region within the detection region, wherein the control section controls the light illuminating section so as to cause light to be illuminated from the light-emitting portions that correspond to the imaging region acquired by the acquisition section.

The fifth aspect of the present invention provides the radiographic imaging device of the fourth aspect, wherein the control section causes at least some of the light-emitting portions that correspond to a non-imaging region to emit light at a light amount lower than a light amount of the light-emitting portions that correspond to the imaging region.

The sixth aspect of the present invention provides the radiographic imaging device of the fourth aspect, wherein the imaging region is made to be an irradiation region at which radiation is irradiated onto the detection region.

The seventh aspect of the present invention provides the radiographic imaging device of the fourth aspect, further including:

a detection section that detects a charge amount due to dark current that is generated at each sensor portion of a non-irradiation region of the imaging panel, wherein the control section controls the light illuminating section such that, the smaller the charge amount due to dark current that is detected by the detection section, the smaller the light amount and illumination time period.

The eighth aspect of the present invention provides the radiographic imaging device of the first aspect, further including:

a battery that at least supplies electric power for driving the imaging panel and electric power for causing the respective light-emitting portions of the light illuminating section to emit light, wherein, when a remaining amount of electric power stored in the battery is less than a predetermined allowed amount, the control section controls the light illuminating section to carry out any of stopping of illumination of, decreasing of a light amount of, and shortening of an illumination time period of light.

The ninth aspect of the present invention provides the radiographic imaging device of the first aspect, wherein when still imaging is to be carried out in the midst of through imaging that carries out imaging continuously, the control section controls the light illuminating section to cause all of the light-emitting portions to emit light at least one of immediately before and immediately after the still imaging.

The tenth aspect of the present invention provides the radiographic imaging device of the first aspect, wherein the actual results of imaging express a portion, within the detection region, at which radiation was irradiated without having passed through a subject in a past image capturing, and the control section controls the light illuminating section such that much light is illuminated onto the portion, within the detection region, at which radiation was irradiated without having passed through the subject.

On the other hand, the eleventh aspect of the present invention provides a radiographic imaging system including:

an imaging panel at which plural sensor portions, that detect radiation or light converted from radiation, are formed at a detection region, and that captures a radiographic image expressed by radiation or light converted from radiation;

a light illuminating section at which plural light-emitting portions, that can individually illuminate light for erasing residual images, are provided per sectional region obtained by dividing an imaging region into plural the sectional regions; and a control section that, in accordance with imaging conditions, controls absence/presence of illumination of, light amount of, and illumination time period of light from the respective light-emitting portions of the light illuminating section.

Accordingly, because the present invention operates in the same way as the first aspect, consumption of electric power can be suppressed while the occurrence of residual images is suppressed.

In accordance with the present invention, the effect is obtained that consumption of electric power can be suppressed while the occurrence of residual images is suppressed.

BRIEF DESCRIPTION OF THE DRAWINGS

Exemplary embodiments of the present invention will be described in detail based on the following figures, wherein:

FIG. 12 is a block diagram showing the structure of main portions of the electrical system of the electronic cassette relating to the exemplary embodiments;

DETAILED DESCRIPTION

Hereinafter, exemplary embodiments for implementing the present invention will be described in detail with reference to the drawings. Note that, here, description is given of an example of a case in which the present invention is applied to a radiographic imaging system that carries out capturing of radiographic images by using an electronic cassette.

[First Exemplary Embodiment]

Figure 1:
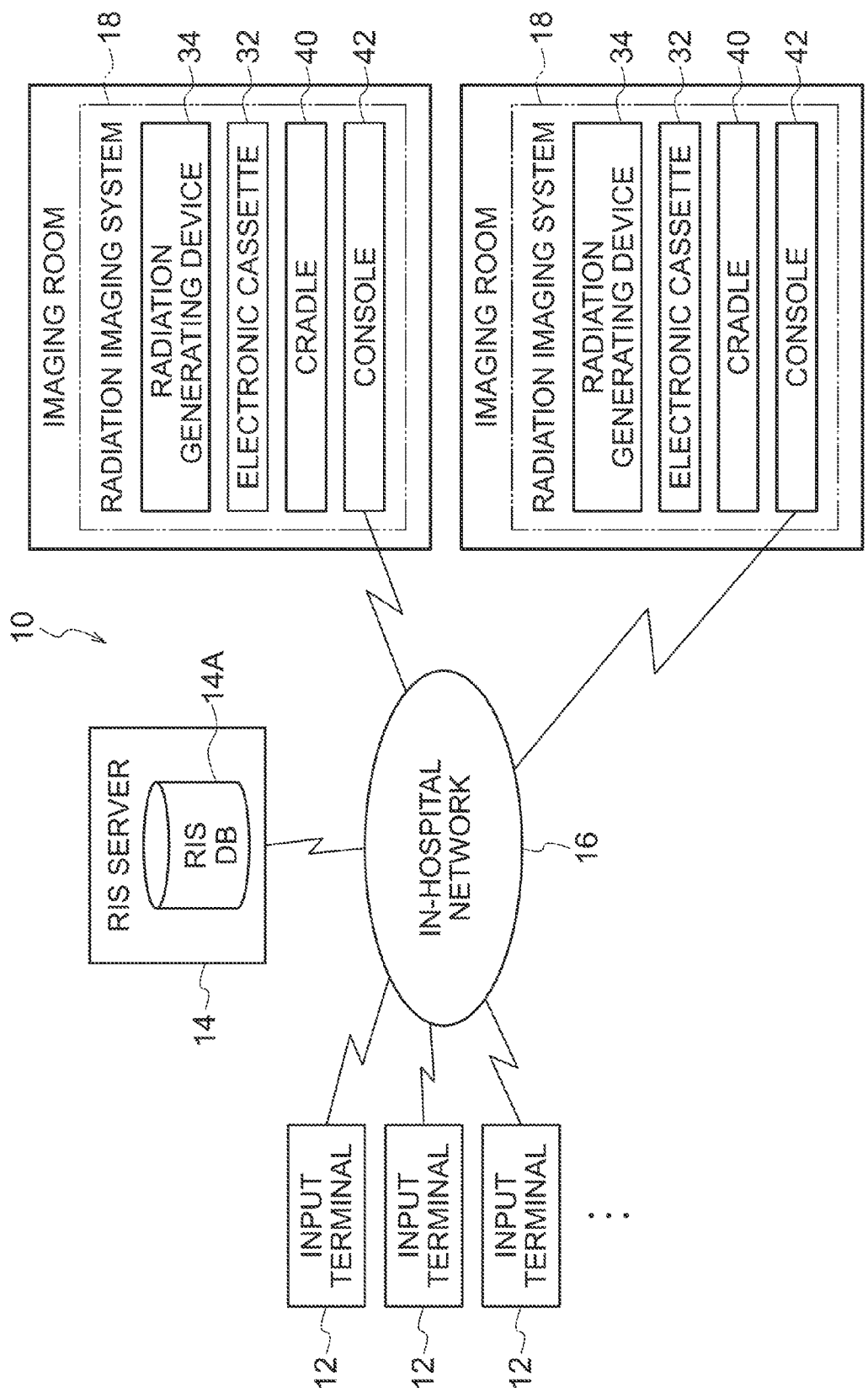
FIG. 1 is a block diagram showing the structure of a radiology information system relating to exemplary embodiments.

First, the structure of a radiology information system (hereinafter called "RIS") 10 relating to the present exemplary embodiment will be described with reference to FIG. 1.

The RIS 10 is a system for carrying out information management such as scheduling of examinations/treatments, recording of diagnoses, and the like in a radiology department, and structures a part of a hospital information system (hereinafter called "HIS").

The RIS 10 has plural imaging requesting terminal devices (hereinafter called "terminal devices") 12, an RIS server 14, and radiographic imaging systems (hereinafter called "imaging systems") 18 that are individually set in radiographic imaging rooms (or operating rooms) within the hospital. The RIS 10 is structured such that these are respectively connected to an in-hospital network 16 that is formed from a wired or wireless LAN (Local Area Network) or the like. Note that the RIS 10 structures a part of the HIS that is provided within the same hospital. An HIS server (not illustrated) that manages the entire HIS also is connected to the in-hospital network 16.

The terminal device 12 is for a doctor or a radiologic technologist to carry out inputting, browsing, and the like of diagnostic information and reservations of facilities. Requests for capturing of radiographic images and reservations for imaging are also made via the terminal device 12. Each of the terminal devices 12 is structured to include a personal computer having a display device, and can communicate back and forth with the RIS server 14 via the in-hospital network 16.

The RIS server 14 accepts imaging requests from the respective terminal devices 12, and manages the imaging schedule of radiographic images at the imaging systems 18. The RIS server 14 is structured to include a database 14A.

The database 14A is structured to include information relating to a patient (subject) such as attribute information (name, sex, birthdate, age, blood type, weight, patient ID, and the like) of the patient, information relating to electronic cassettes 32 that are described hereinafter and that are used in the imaging systems 18 such as the identification numbers (ID information), types, sizes and the like of the electronic cassettes 32, and environment information showing the environments in which radiographic images are captured by using the electronic cassettes 32, i.e., environments in which the electronic cassettes 32 are used (as examples, a radiographic imaging room, an operating room, or the like).

The imaging system 18 carries out capturing of radiographic images by the operation of an operator, such as a doctor or a radiologic technologist or the like, in accordance with instructions from the RIS server 14. The imaging system 18 has: a radiation generating device 34 that irradiates, from a radiation source 130 (see FIG. 2 as well) and onto a subject, radiation X (see FIG. 3 as well) of a radiation amount according to exposure conditions; the electronic cassette 32 that incorporates therein a radiation detector 60 (see FIG. 3 as well) that absorbs the radiation X that has been transmitted through the part to be imaged of the subject, and generates charges, and, on the basis of the generated charge amount, generates image information expressing a radiographic image; a cradle 40 that charges a battery that is incorporated in the electronic cassette 32; and a console 42 that controls the electronic cassette 32, the radiation generating device 34, and the cradle 40.

Figure 2:
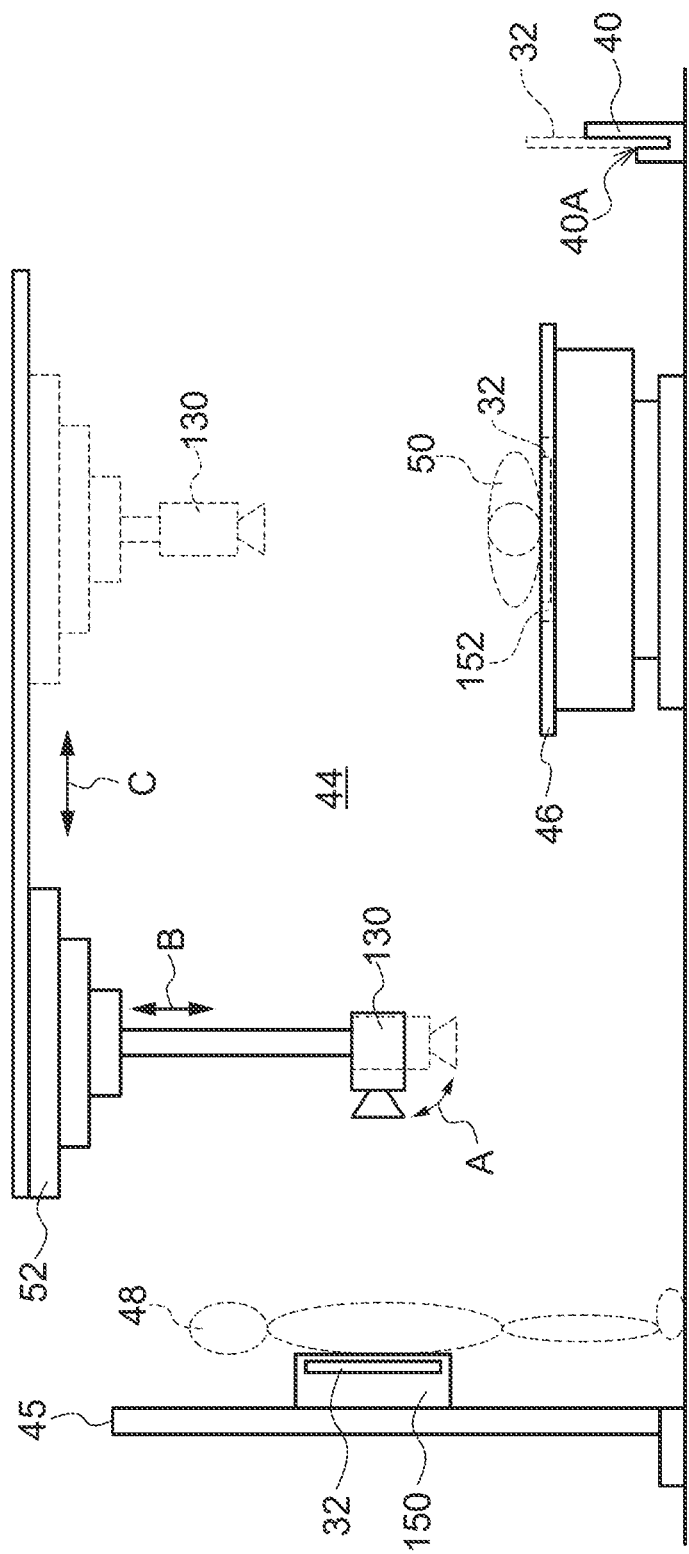
FIG. 2 is a side view showing an example of a state of arrangement of respective devices in a radiographic imaging room of the radiology information system relating to the exemplary embodiments.

FIG. 2 illustrates an example of the arranged state of respective devices, in a radiographic imaging room 44, of the imaging system 18 relating to the present exemplary embodiment.

As shown in FIG. 2, a standing position stand 45, that is used when carrying out radiographic imaging in a standing position, and a supine position stand 46, that is used when carrying out radiographic imaging in a supine position, are set in the radiographic imaging room 44. The space in front of the standing position stand 45 is an imaging position 48 for the subject when radiographic imaging in the standing position is carried out. The space above the supine position stand 46 is an imaging position 50 for the subject when radiographic imaging in the supine position is carried out.

A holding portion 150 that holds the electronic cassette 32 is provided at the standing position stand 45. The electronic cassette 32 is held at the holding portion 150 when capturing of a radiographic image is carried out in the standing position. Similarly, a holding portion 152 that holds the electronic cassette 32 is provided at the supine position stand 46. The electronic cassette 32 is held at the holding portion 152 when capturing of a radiographic image is carried out in the supine position.

Further, a supporting/moving mechanism 52, that supports the radiation source 130 such that the radiation source 130 is rotatable around a horizontal axis (the direction of arrow A in FIG. 2), is movable in the vertical direction (the direction of arrow B in FIG. 2), and is movable in the horizontal direction (the direction of arrow C in FIG. 2), is provided in the radiographic imaging room 44 in order to make both radiographic imaging in the standing position and radiographic imaging in the supine position possible by radiation from the single radiation source 130. Here, the supporting/moving mechanism 52 respectively has a driving source that rotates the radiation source 130 around the horizontal axis, a driving source that moves the radiation source 130 in the vertical direction, and a driving source that moves the radiation source 130 in the horizontal direction (none of these driving sources is illustrated).

On the other hand, an accommodating portion 40A, in which the electronic cassette 32 can be stored, is formed in the cradle 40.

At times of non-use, the battery incorporated in the electronic cassette 32 is charged in a state in which the electronic cassette 32 is stored in the accommodating portion 40A of the cradle 40. At times of capturing radiographic images, the electronic cassette 32 is taken-out from the cradle 40 by the radiology technician or the like, and is held at the holding portion 150 of the standing position stand 45 if the imaging posture is standing, or is held at the holding portion 152 of the supine position stand 46 if the imaging posture is supine.

Here, at the imaging system 18 relating to the present exemplary embodiment, the radiation generating device 34 and the console 42 are respectively connected by a cable, and transmission and receipt of various types of information therebetween is carried out by wired communication. However, the cable that connects the radiation generating device 34 and the console 42 is omitted from FIG. 2. Further, transmission and receipt of various types of information between the electronic cassette 32 and the console 42 is carried out by wireless communication. Note that the communication between the radiation generating device 34 and the console 42 as well may be carried out by wireless communication.

Note that the electronic cassette 32 is not used only in a state of being held at the holding portion 150 of the standing position stand 45 or at the holding portion 152 of the supine position stand 46. Owing to the portability thereof, the electronic cassette 32 can also be used in a state of not being held at a holding portion.

Figure 3:
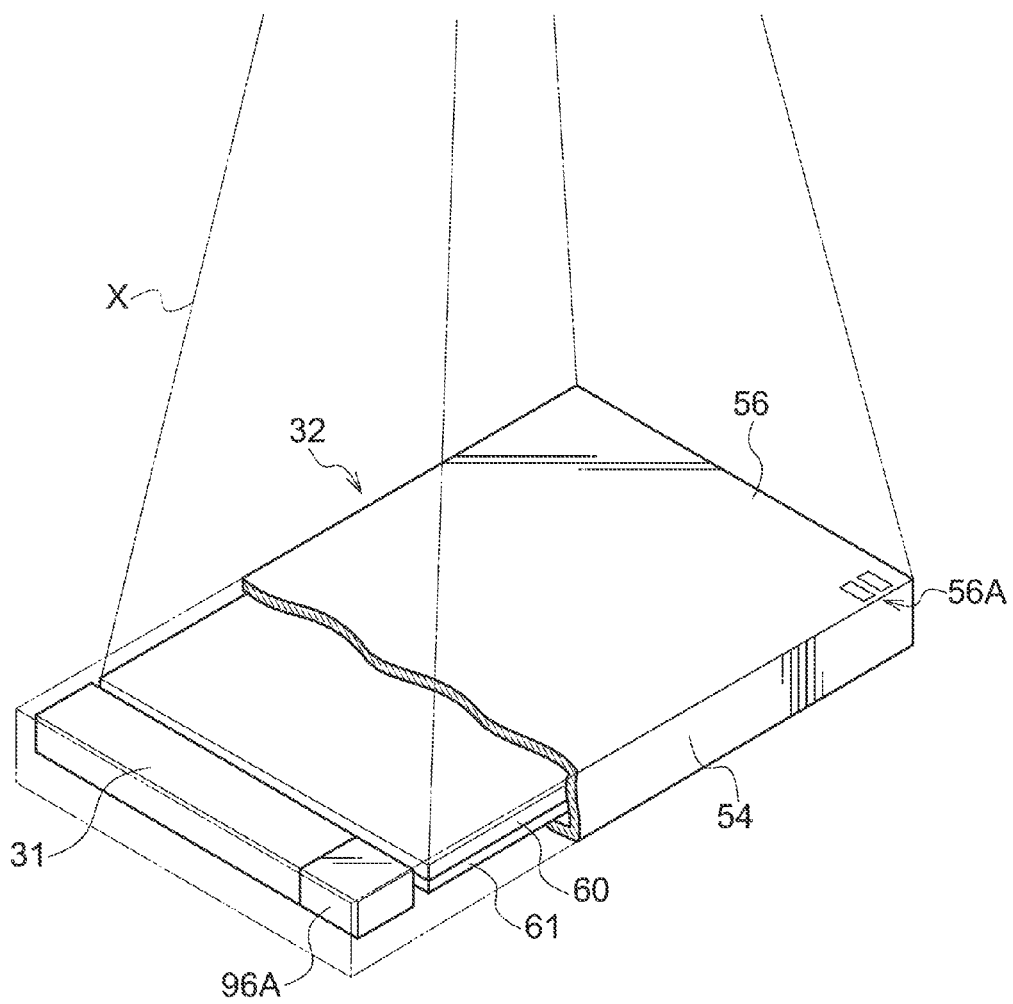
FIG. 3 is a transparent perspective view showing the internal structure of an electronic cassette relating to the exemplary embodiments.

The internal structure of the electronic cassette 32 relating to the present exemplary embodiment is shown in FIG. 3.

As shown in FIG. 3, the electronic cassette 32 has a housing 54 formed from a material through which the radiation X is transmitted, and is a structure that is waterproof and airtight. When the electronic cassette 32 is being used in an operating room or the like, there is the concern that blood or other various germs will stick thereto. Thus, by making the electronic cassette 32 be a waterproof and airtight structure and disinfectingly cleaning it as needed, the one electronic cassette 32 can be used repeatedly in continuation.

The radiation detector 60 that captures a radiographic image formed by the radiation X, and a light-emitting panel 61 that generates light that erases residual images of the radiation detector 60, are disposed within the housing 54 in that order from an image-capturing surface 56 side of the housing 54 on which the radiation X that has passed through the subject is irradiated.

A case 31, that accommodates electronic circuits including a microcomputer and accommodates a battery 96A that is chargeable and attachable/detachable, is disposed at one end side of the interior of the housing 54. The radiation detector 60 and the electronic circuits are operated by electric power that is supplied from the battery 96A disposed in the case 31. In order to avoid damage, that accompanies irradiation of the radiation X, to the various types of circuits that are accommodated within the case 31, it is desirable to place a lead plate or the like at the image-capturing surface 56 side of the case 31. Note that the electronic cassette 32 relating to the present exemplary embodiment is a parallelepiped at which the shape of the image-capturing surface 56 is rectangular, and the case 31 is disposed at one end portion in the longitudinal direction thereof.

A display portion 56A, that carries out display showing the operating state of the electronic cassette 32 such the operating mode that is a "ready state" or "currently transmitting data", and the state of the remaining capacity of the battery 96A, and the like, is provided at a predetermined position of an outer wall of the housing 54. Note that, although light-emitting diodes are used as the display portion 56A at the electronic cassette 32 relating to the present exemplary embodiment, the display portion 56A is not limited to the same, and may be light-emitting elements other than light-emitting diodes, or may be another display means such as a liquid crystal display, an organic EL display, or the like.

Figure 4:
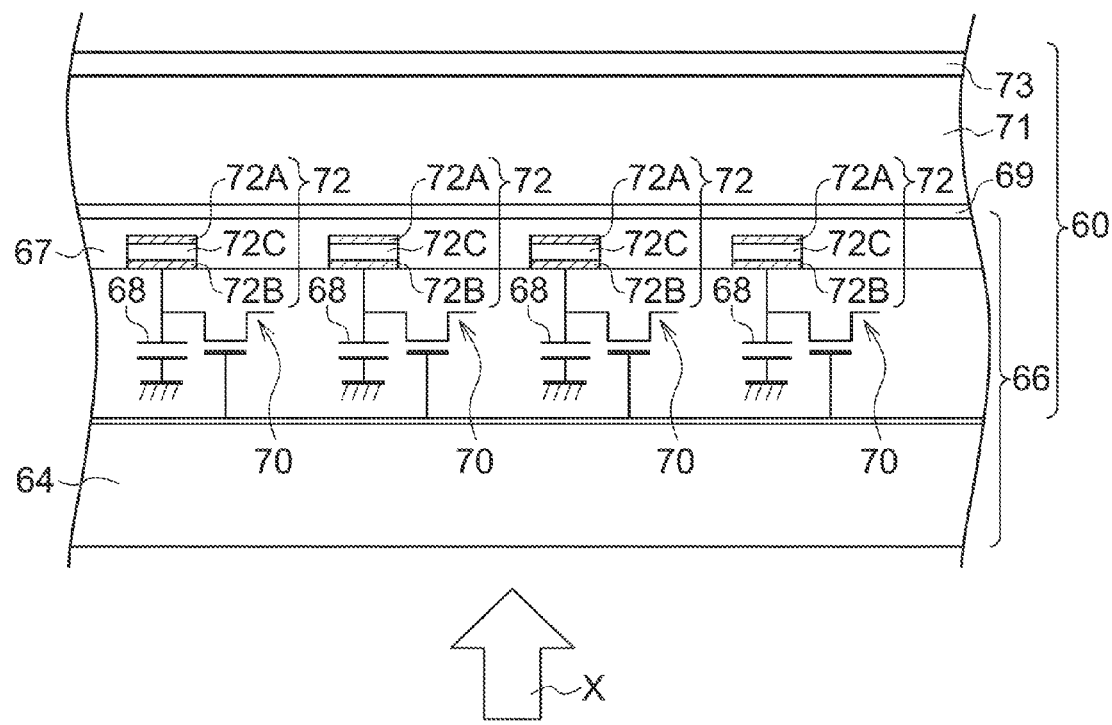
FIG. 4 is a sectional view schematically showing the structure of a radiation detector relating to the exemplary embodiments.

A sectional view schematically showing the structure of the radiation detector 60 relating to the present exemplary embodiment is shown in FIG. 4.

The radiation detector 60 has a TFT active matrix substrate (hereinafter called "TFT substrate") 66 at which thin film transistors (hereinafter called "TFTs") 70 and storage capacitors 68 are formed at an insulating substrate 64.

A scintillator 71, that converts incident radiation into light, is disposed on the TFT substrate 66.

For example, CsI:Tl or GOS ($Gd_2O_2S$:Tb) can be used as the scintillator 71. Note that the scintillator 71 is not limited to these materials.

The insulating substrate 64 may be any substrate provided that it is light-transmissive and there is little absorption of radiation thereat, and, for example, a glass substrate, a transparent ceramic substrate, or a light-transmissive resin substrate can be used therefore. Note that the insulating substrate 64 is not limited to these materials.

The wavelength region of the light that the scintillator 71 generates is preferably the visible light region (wavelengths of 360 nm to 830 nm). It is more preferable that the green wavelength region be included in order to enable monochromatic imaging by the radiation detector 60.

When imaging is carried out by using X-rays as the radiation, concretely, a phosphor that contains cesium iodide (CsI) is preferable as the phosphor used in the scintillator 71, and use of CsI(Tl), whose emission spectrum at the time of X-ray irradiation is within 420 nm to 700 nm, is particularly preferable. Note that the emission peak wavelength in the visible light region of CsI(Tl) is 565 nm.

When the scintillator 71 is to be formed by, for example, columnar crystals of CsI(Tl) or the like, the scintillator 71 may be formed by vapor deposition onto a vapor deposition substrate. When the scintillator 71 is formed by vapor deposition in this way, a plate of Al is often used as the vapor deposition substrate from the standpoints of X-ray transmittance and cost, but the material of the vapor deposition substrate is not limited to this. Note that, when GOS is used as the scintillator 71, the scintillator 71 may be formed by coating GOS on the surface of the TFT substrate 66, without using a vapor deposition substrate.

Sensor portions 72, that generate charges due to light converted by the scintillator 71 being incident thereon, are formed at the TFT substrate 66. Further, a planarizing layer 67 for planarizing the top side of the TFT substrate 66 is formed at the TFT substrate 66. An adhesive layer 69 for adhering the scintillator 71 to the TFT substrate 66 is formed on the planarizing layer 67, between the TFT substrate 66 and the scintillator 71.

The sensor portion 72 has an upper electrode 72A, a lower electrode 72B, and a photoelectric converting film 72C that is disposed between the upper and lower electrodes.

The upper electrode 72A and the lower electrode 72B are formed by using a material having high light transmittance, such as ITO (indium tin oxide) or IZO (indium zinc oxide) or the like, and are light-transmissive.

The photoelectric converting film 72C absorbs light emitted from the scintillator 71, and generates charges that correspond to the absorbed light. It suffices for the photoelectric converting film 72C to be formed from a material that generates charges due to light being illuminated thereon, and, for example, can be formed from amorphous silicon or an organic photoelectric converting material or the like. In the case of the photoelectric converting film 72C that contains amorphous silicon, the photoelectric converting film 72C has a broad absorption spectrum and can absorb light emitted by the scintillator 71. In the case of the photoelectric converting film 72C that contains an organic photoelectric converting material, the photoelectric converting film 72C has a sharp absorption spectrum in the visible region, and hardly any electromagnetic waves other than the light emitted by the scintillator 71 are absorbed at the photoelectric converting film 72C, and generated noise can be effectively suppressed by radiation such as X-rays or the like being absorbed at the photoelectric converting film 72C.

In order for the organic photoelectric converting material that structures the photoelectric converting film 72C to most efficiently absorb light emitted at the scintillator 71, it is preferable that the absorption peak wavelength thereof be closer to the emission peak wavelength of the scintillator 71. Although it is ideal for the absorption peak wavelength of the organic photoelectric converting material and the emission peak wavelength of the scintillator 71 to match, if the difference therebetween is small, light emitted from the scintillator 71 can be absorbed sufficiently. Concretely, the difference between the absorption peak wavelength of the organic photoelectric converting material and the emission peak wavelength with respect to radiation of the scintillator 71 is preferably within 10 nm, and more preferably within 5 nm.

In the present exemplary embodiment, the photoelectric converting film 72C is structured to contain an organic photoelectric converting material. Quinacridone-based organic compounds and phthalocyanine-based organic compounds are examples of the organic photoelectric converting material. For example, because the absorption peak wavelength in the visible region of quinacridone is 560 nm, if quinacridone is used as the organic photoelectric converting material and CsI(Tl) is used as the material of the scintillator 71, it is possible for the aforementioned difference in peak wavelengths to be kept within 5 nm, and the charge amount generated at the photoelectric converting film 72C can be made to be the substantial maximum. Organic photoelectric converting materials that can be used as the photoelectric converting film 72C are described in detail in JP-A No. 2009-32854, and therefore, description thereof is omitted here.

Figure 5:
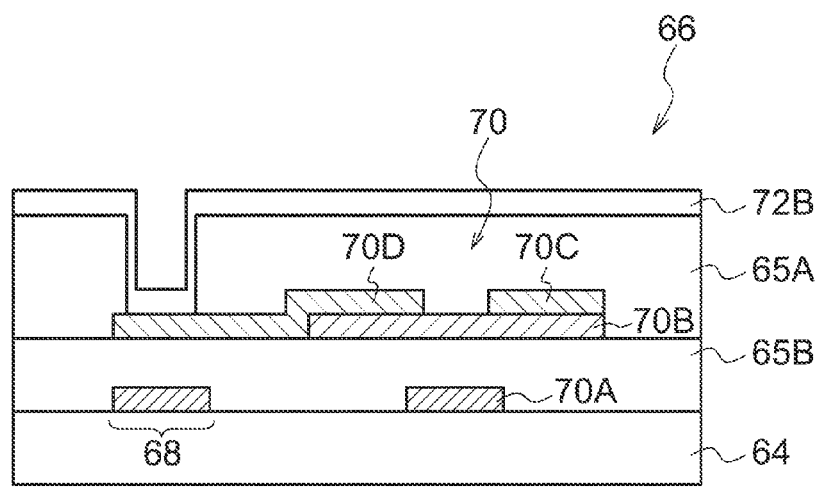
FIG. 5 is a sectional view showing the structures of a thin film transistor and a capacitor of the radiation detector relating to the exemplary embodiments.

The structure of the TFT 70 and the storage capacitor 68 that are formed at the TFT substrate 66 relating to the present exemplary embodiment is shown schematically in FIG. 5.

The storage capacitors 68, that accumulate the charges that moved to the lower electrodes 72B, and the TFTs 70, that convert the charges accumulated in the storage capacitors 68 into electric signals and output the electric signals, are formed on the insulating substrate 64 in correspondence with the lower electrodes 72B. The region at which the storage capacitor 68 and the TFT 70 are formed has a portion that overlaps the lower electrode 72B in plan view. Due to such a structure, the storage capacitor 68 and the TFT 70, and the sensor portion 72 at each pixel portion overlap in the thickness direction, and the storage capacitor 68 and the TFT 70, and the sensor portion 72 can be disposed in a small surface area.

The storage capacitor 68 is electrically connected to the corresponding lower electrode 72B via a wire that is made of an electrically conductive material and is formed so as to pass through an insulating film 65A that is provided between the insulating substrate 64 and the lower electrode 72B. Due thereto, the charges that have been caught at the lower electrode 72B can be moved to the storage capacitor 68.

At the TFT 70, a gate electrode 70A, a gate insulating film 65B and an active layer (channel layer) 70B are layered. Further, a source electrode 70C and a drain electrode 70D are formed on the active layer 70B with a predetermined interval therebetween.

The active layer 70B can be formed from, for example, amorphous silicon, an amorphous oxide, an organic semiconductor material, carbon nanotubes, or the like. Note that the material that structures the active layer 70B is not limited to these.

As amorphous oxides that structure the active layer 70B, oxides containing at least one of In, Ga and Zn (e.g., In—O type) are preferable, and oxides containing at least two of In, Ga and Zn (e.g., In—Zn—O type, In—Ga—O type, Ga—Zn—O type) are more preferable, and oxides containing In, Ga and Zn are particularly preferable. As In—Ga—Zn—O type amorphous oxides, amorphous oxides whose composition in a crystalline state is expressed by $InGaO_3(ZnO)_m$ (where m is a natural number of less than 6) are preferable, and in particular, $InGaZnO_4$ is more preferable.

Phthalocyanine compounds, pentacene, vanadyl phthalocyanine, and the like are examples of organic semiconductor materials that can structure the active layer 70B, but the organic semiconductor materials are not limited to these. Note that structures of phthalocyanine compounds are described in detail in JP-A No. 2009-212389, and therefore, description thereof is omitted here.

If the active layer 70B of the TFT 70 is formed by an amorphous oxide, an organic semiconductor material, or carbon nanotubes, radiation such as X-rays or the like is not absorbed, or, even if radiation is absorbed, the absorption is limited to an extremely small amount, and therefore, the generation of noise at the TFT 70 can be effectively suppressed.

Further, when the active layer 70B is formed by carbon nanotubes, the switching speed of the TFT 70 can be made to be high-speed, and further, the TFT 70 that has a low absorption rate of light in the visible light region can be formed. Note that, when the active layer 70B is formed by carbon nanotubes, the performance of the TFT 70 markedly deteriorates merely due to an extremely small amount of metal impurities being mixed in the active layer 70B, and therefore, the active layer 70B must be formed by separating and extracting carbon nanotubes of extremely high purity by centrifugal separation or the like.

Here, with all of the aforementioned amorphous oxides, organic semiconductor materials, carbon nanotubes and organic photoelectric converting materials, film formation at a low temperature is possible. Accordingly, the insulating substrate 64 is not limited to substrates that are highly heat-resistant such as quartz substrates, glass substrates and the like, and flexible substrates of plastic or the like, and aramid and bio-nanofibers can also be used. Concretely, flexible substrates of polyesters such as polyethylene terephthalate, polybutylene phthalate, polyethylene naphthalate and the like, and polystyrene, polycarbonate, polyethersulfone, polyarylate, polyimide, polycycloolefin, norbornene resins, poly(chlorotrifluoroethylene) and the like can be used. If such a flexible substrate made of plastic is used, lightening of weight can be achieved, which is advantageous in terms of, for example, portability and the like. Note that an insulating layer for ensuring the insulating ability, a gas barrier layer for preventing passage of moisture and oxygen, an undercoat layer for improving smoothness and a tight fit with the electrodes and the like, or the like may be provided at the insulating substrate 64.

With aramid, high-temperature processes of greater than or equal to 200° can be applied, and therefore, a transparent electrode material can be cured at a high temperature and made to be low resistance. Further, aramid is suitable also for automatic packaging of a driver IC, including the solder reflow process. Moreover, because the thermal expansion coefficient of aramid is close to those of ITO (indium tin oxide) and glass substrates, there is little warping after manufacture, and aramid is difficult to break. Further, aramid can form substrates that are thin as compared with glass substrates or the like. Note that the insulating substrate 64 may be formed by layering an ultra-thin glass substrate and aramid.

Bio-nanofibers are fibers in which a cellulose microfibril bundle (bacteria cellulose) that produces bacteria (acetic acid bacterium, *Acetobacter Xylinum*), and a transparent resin are compounded. When the cellulose microfibril bundle has a width of 50 nm, the cellulose microfibril bundle is a size of 1/10 with respect to the visible light wavelength, and has high strength, high elasticity, and low thermal expansion. By impregnating and hardening a transparent resin, such as an acrylic resin, an epoxy resin or the like, in bacteria cellulose, bio-nanofibers that exhibit light transmittance of about 90% at a wavelength of 500 nm while containing up to 60 to 70% fiber, are obtained. Bio-nanofibers have a low thermal expansion coefficient (3-7 ppm) that is comparable to that of silicon crystal, have strength (460 MPa) to the same extent as that of steel, have high elasticity (30 GPa), and are flexible. Therefore, the insulating substrate 64 can be formed to be thin as compared with a glass substrate or the like.

Figure 6:
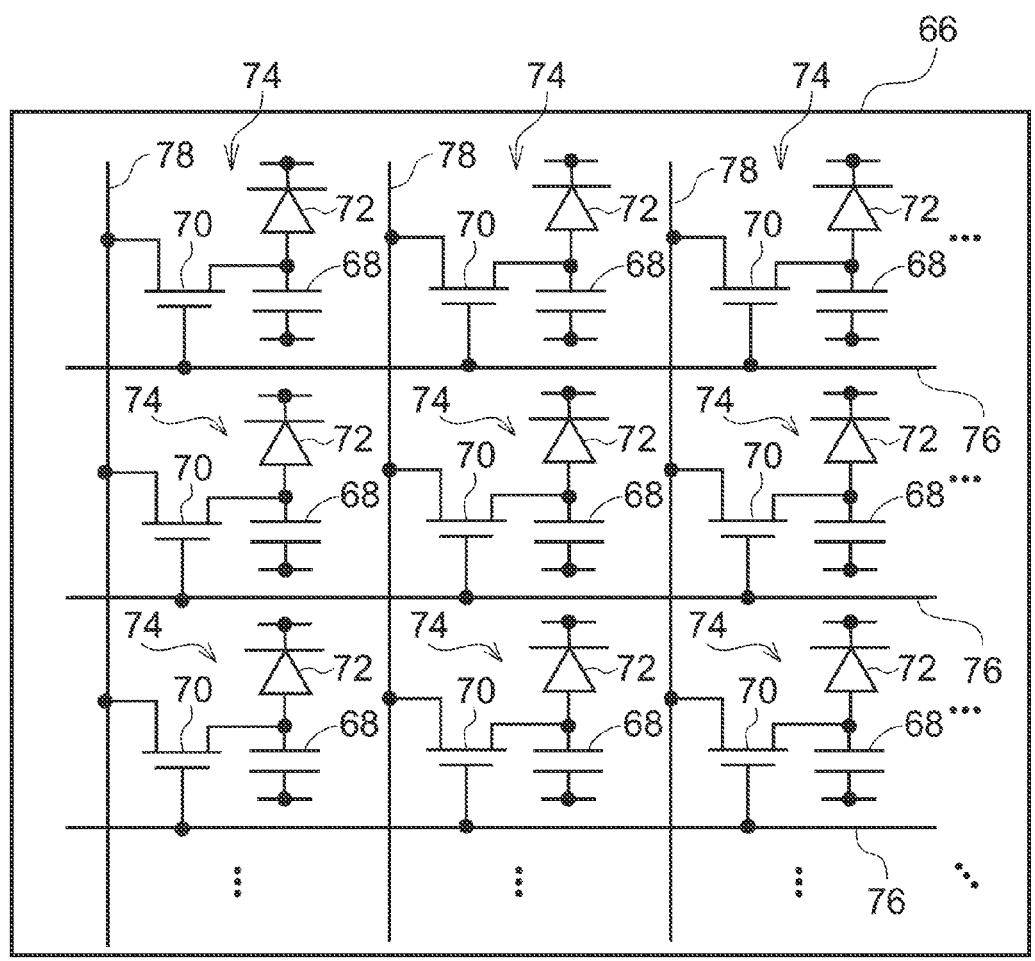
FIG. 6 is a plan view showing the structure of a TFT substrate relating to the exemplary embodiments.

A plan view showing the structure of the TFT substrate 66 relating to the present exemplary embodiment is shown in FIG. 6.

Plural pixels 74, that are structured to include the above-described sensor portions 72, storage capacitors 68 and TFTs 70, are provided at the TFT substrate 66 in a two-dimensional form in a given direction (the row direction in FIG. 6) and in a direction (the column direction in FIG. 6) intersecting the given direction.

Plural gate lines 76 that extend in the given direction (the row direction) and are for turning the respective TFTs 70 on and off, and plural data lines 78 that extend in the intersecting direction (the column direction) and are for reading-out charges via the TFTs 70 that are in on states, are provided at the TFT substrate 66.

The radiation detector 60 is flat-plate shaped, and, in plan view, forms a quadrilateral shape having four sides at the outer edge thereof. Concretely, the radiation detector 60 is formed in a rectangular shape.

As shown in FIG. 4, the radiation detector 60 relating to the present exemplary embodiment is formed by the scintillator 71 being affixed to the surface of this TFT substrate 66.

When the scintillator 71 is to be formed of, for example, columnar crystals of CsI:Tl or the like, the scintillator 71 is formed by vapor deposition onto a vapor deposition substrate 73. Note that, when GOS is used as the scintillator 71, the scintillator 71 may be formed by coating GOS on the surface of the TFT substrate 66, without using the vapor deposition substrate 73.

Figure 7:
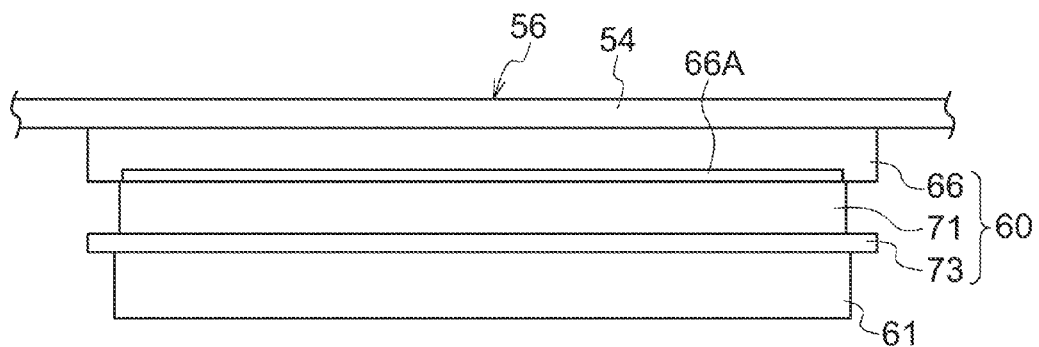
FIG. 7 is a side view showing the structure of the interior of the electronic cassette relating to the exemplary embodiments.

FIG. 7 is a side view showing the arranged structure of the radiation detector 60 within the electronic cassette 32 relating to the present exemplary embodiment. Note that, in FIG. 7, in order to make it easy to identify a detection region 66A of the TFT substrate 66 at which the plural pixels 74 are provided in a two-dimensional form, the detection region 66A is illustrated as a layer.

Within the electronic cassette 32, the radiation detector 60 is affixed to the top plate portion that structures the image-capturing surface 56 of the housing 54, such that the TFT substrate 66 side becomes the top plate side.

Figure 8:
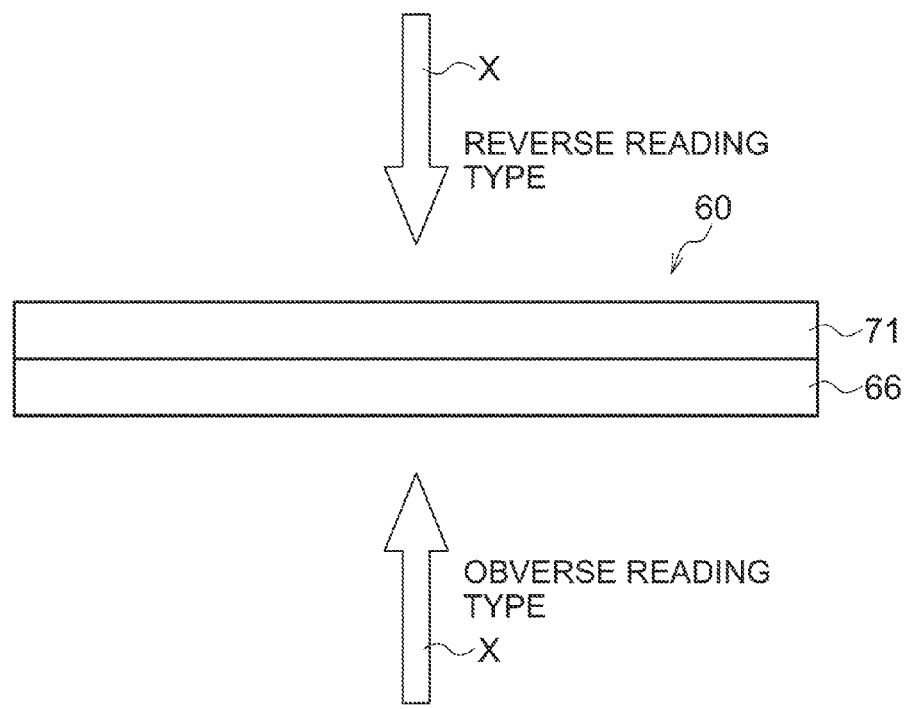
FIG. 8 is a sectional side view for explaining an obverse reading method and a reverse reading method.

Here, as shown in FIG. 8, when the radiation detector 60 is a so-called reverse reading type (a so-called PSS (Penetration Side Sampling) type) in which radiation is irradiated from the side at which the scintillator 71 is formed and the radiographic image is read from the TFT substrate 66 that is provided at the reverse surface side of the incident surface of the radiation, light is emitted more strongly at the top surface side, in the drawing, of the scintillator 71 (the side opposite the TFT substrate 66). When the radiation detector 60 is a so-called obverse reading type (a so-called ISS (Irradiation Side Sampling) type) in which radiation is irradiated from the TFT substrate 66 side and the radiographic image is read from the TFT substrate 66 that is provided at the obverse surface side of the incident surface of the radiation, the radiation that has passed through the TFT substrate 66 is incident on the scintillator 71, and the TFT substrate 66 side of the scintillator 71 emits light more strongly. At the respective sensor portions 72 that are provided at the TFT substrate 66, charges are generated by the light generated at the scintillator 71. Therefore, when the radiation detector 60 is an obverse reading type, the light emitting position of the scintillator 71 with respect to the TFT substrate 66 is closer and therefore the resolution of the radiographic image obtained by imaging is higher, than when the radiation detector 60 is a reverse reading type.

In the present exemplary embodiment, as shown in FIG. 7, the radiation detector 60 is affixed to the top plate portion that structures the image-capturing surface 56 of the housing 54, such that the TFT substrate 66 side becomes the top plate side. Due thereto, a high-resolution radiographic image can be captured.

The light-emitting panel 61 is disposed at the scintillator 71 side surface of this radiation detector 60.

Figure 9:
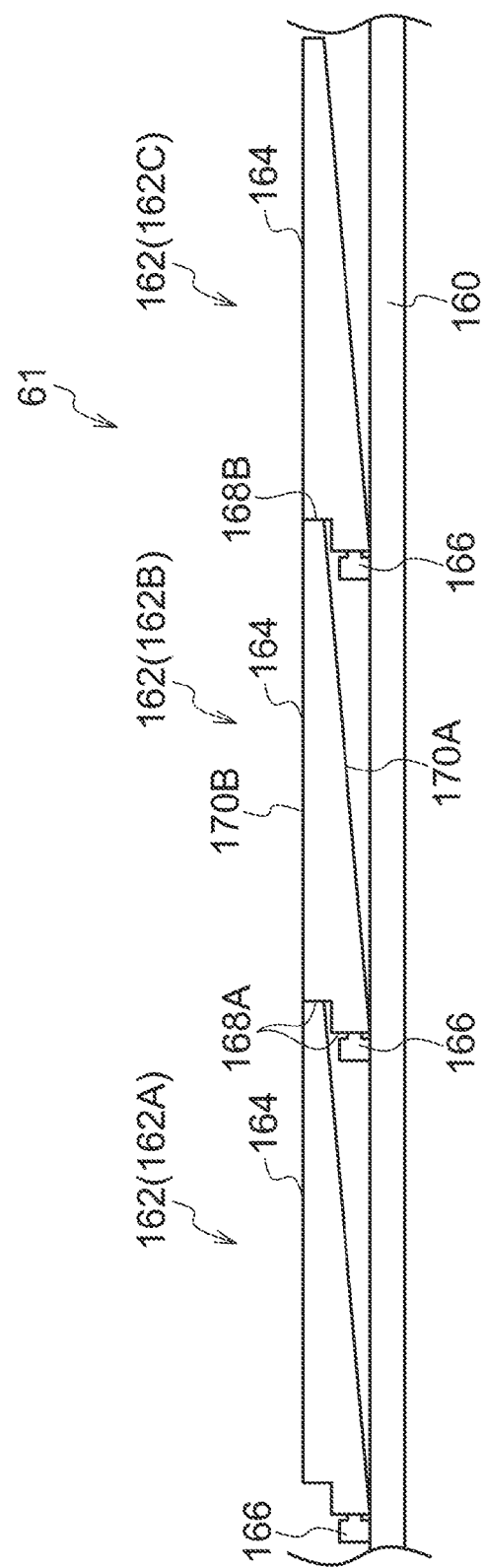
FIG. 9 is a sectional view schematically showing the structure of a light-emitting panel relating to the exemplary embodiments.

A sectional view schematically showing the structure of the light-emitting panel 61 relating to the present exemplary embodiment is shown in FIG. 9.

At the light-emitting panel 61, for example, plural light-emitting portions 162 that can emit light individually are disposed on a supporting substrate 160. A light guiding plate 164 that is shaped as a flat plate and rectangular, and a light-emitting element 166 such as a light-emitting diode or the like that illuminates light toward the light guiding plate 164, are provided at each of the light-emitting portions 162.

The light guiding plate 164 is formed by one surface 170A being inclined such that one side surface 168A side of the light guiding plate 164 is thick and a side surface 168B side at the side opposite the side surface 168A becomes thinner. The corner portion at another surface 170B side of the side surface 168A of the light guiding plate 164 is sunken-in, such that a step is provided at the surface 170B side of the side surface 168A. Each of the waveguide plates 164 is disposed such that the thin side surface 168B overlaps the sunken-in portion of the step of the side surface 168A of the adjacent light guiding plate 164. Each of the light-emitting elements 166 is disposed at the convex portion of the step of the light guiding plate 164, so as to overlap the adjacent light guiding plate 164. The light from the light-emitting element 166 that is provided at the side surface 168A is incident on that light guiding plate 164.

There is no need for the light-emitting portions 162 of the light-emitting panel 61 to be formed as finely as the sensor portions 72 that are provided at the respective pixels 74 of the radiation detector 60. The light-emitting portions 162 may be formed to be larger than the sensor portions 72, and may be formed to a size of from several tens to several hundreds of pixels of the radiation detector 60.

Figure 10:
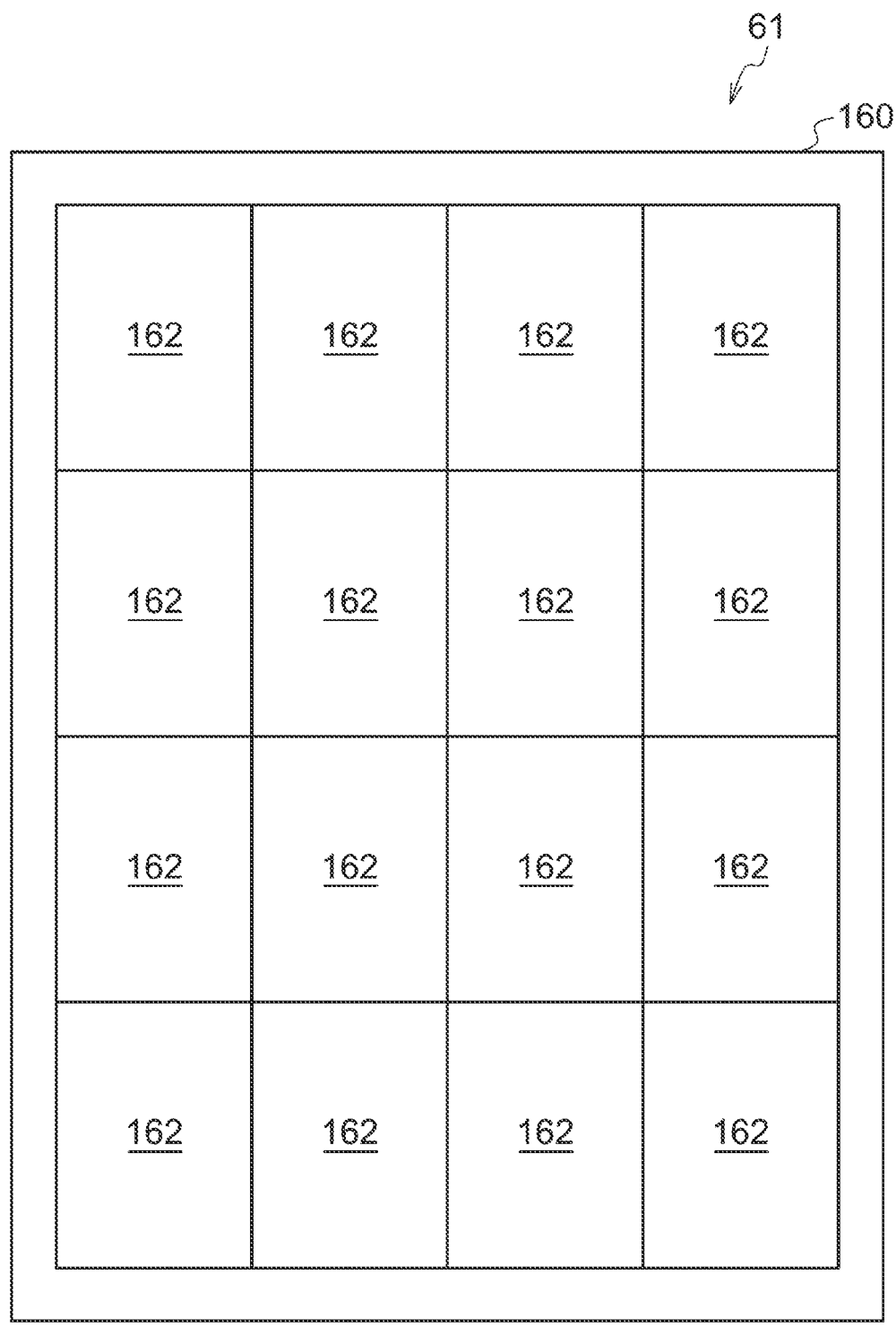
FIG. 10 is a plan view showing the arranged structure of light-emitting portions of the light-emitting panel relating to the exemplary embodiments.

A plan view showing the arranged structure of the light-emitting portions 162 of the light-emitting panel 61 relating to the present exemplary embodiment is shown in FIG. 10.

A large number of the light-emitting portions 162 are disposed at the light-emitting panel 61 in a given direction (the row direction in FIG. 10) and in a direction (the column direction in FIG. 10) intersecting the given direction. For example, the light-emitting portions 162 are arranged in the form of a matrix with four each in the row direction and the column direction.

The light-emitting area over which light is emitted by the plural light-emitting portions 162 of the light-emitting panel 61 is made to be a size that is larger than the rectangular detection region 66A, at which the plural pixels 74 are provided in a two-dimensional form, of the TFT substrate 66.

Figure 11A:
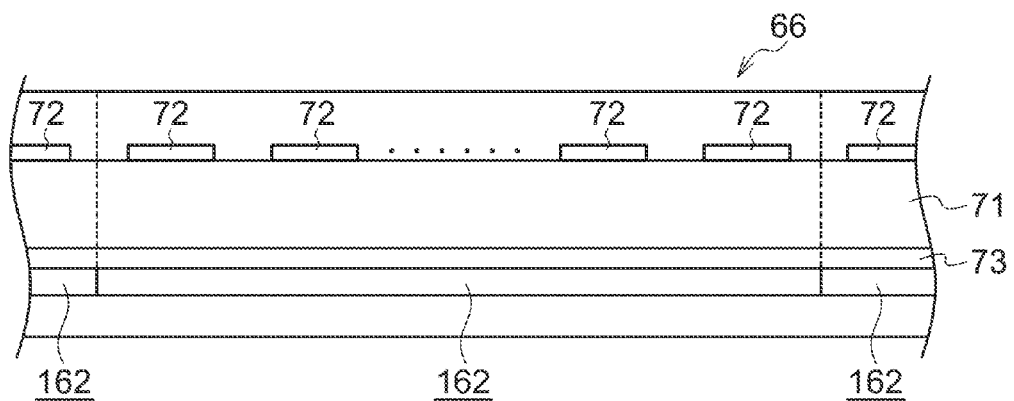
FIG. 11A is a sectional view showing an arranged structure in which the light-emitting panel is arranged such that borders of the respective light-emitting portions are positioned between sensor portions of the TFT substrate.

In the present exemplary embodiment, the vapor deposition substrate 73 of the scintillator 71 is made to be a substrate that is light-transmissive, such as a glass substrate or the like. As shown in FIG. 11A, the light-emitting panel 61 is disposed such that the light-emitting portions 162 face the vapor deposition substrate 73 side of the radiation detector 60.

Figure 11B:
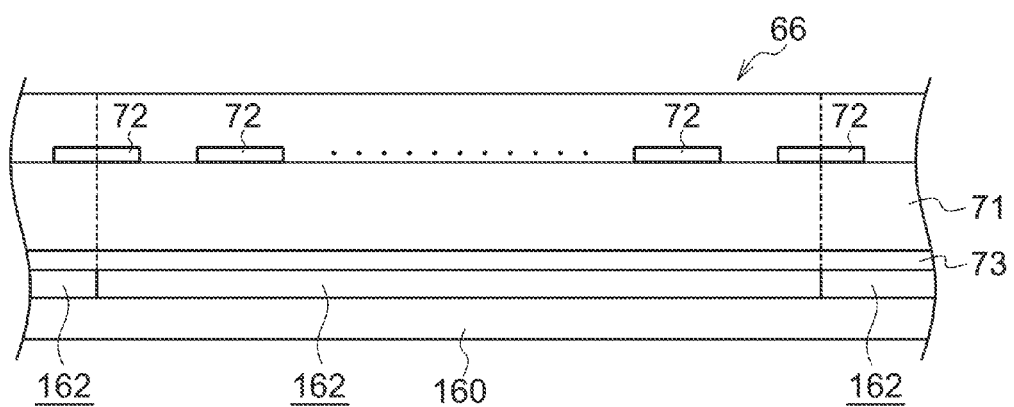
FIG. 11B is a sectional view showing an arranged structure in which the light-emitting panel is arranged such that borders of the respective light-emitting portions are positioned on the sensor portions of the TFT substrate.

Note that the respective light-emitting portions 162 of the light-emitting panel 61 may be disposed such that the borders between the respective light-emitting portions 162 are positioned between the sensor portions 72 of the TFT substrate 66 as shown in FIG. 11A, or may be disposed such that the borders of the respective light-emitting portions 162 are on the sensor portions 72 of the TFT substrate 66 as shown in FIG. 11B. By arranging the light-emitting portions 162 such that the borders of the respective light-emitting portions 162 are on the sensor portions 72 of the TFT substrate 66, lights from two of the light-emitting portions 162 are illuminated onto the sensor portions 72 at the borders of the light-emitting portions 162, and therefore, it is possible to suppress steps from arising at the positions that are the borders of the light-emitting portions 162 in the radiographic image captured by the radiation detector 60.

A block diagram showing the structure of main portions of the electrical system of the electronic cassette 32 relating to a first exemplary embodiment is shown in FIG. 12.

As described above, the numerous pixels 74, which are provided with the sensor portions 72, the storage capacitors 68 and the TFTs 70, are arranged in the form of a matrix at the radiation detector 60. The charges, which are generated at the sensor portions 72 accompanying the irradiation of the radiation X onto the electronic cassette 32, are accumulated in the storage capacitors 68 of the individual pixels 74. Due thereto, the image information, which is carried by the radiation X that was irradiated onto the electronic cassette 32, is converted into charge information and held at the radiation detector 60.

Further, the individual gate lines 76 of the radiation detector 60 are connected to a gate line driver 80, and the individual data lines 78 are connected to a signal processing section 82. When charges are accumulated in the storage capacitors 68 of the individual pixels 74, the TFTs 70 of the individual pixels 74 are turned on in order in units of a row by signals supplied from the gate line driver 80 via the gate lines 76, and the charges, that are accumulated in the storage capacitors 68 of the pixels 74 at which the TFTs 70 have been turned on, are transferred through the data lines 78 as analog electric signals, and are inputted to the signal processing section 82. Accordingly, the charges accumulated in the storage capacitors 68 of the individual pixels 74 are read-out in order in row units.

The signal processing section 82 has an amplifier and a sample/hold circuit for each of the individual data lines 78. The electric signals transferred through the individual data lines 78 are amplified at the amplifiers, and thereafter, are held by the sample/hold circuits. A multiplexer and an A/D (analog/digital) converter are connected in that order to the output sides of the sample/hold circuits. The electric signals held in the individual sample/hold circuits are inputted in order (serially) to the multiplexer, and are converted into digital data by the A/D converter.

An image memory 90 is connected to the signal processing section 82. The digital data outputted from the A/D converter of the signal processing section 82 is stored in order in the image memory 90. The image memory 90 has a storage capacity that can store image data of an amount corresponding to plural frames. Each time capturing of a radiographic image is carried out, the digital data of the respective pixels 74 of the radiation detector 60 are successively stored as image data in the image memory 90.

The image memory 90 is connected to a cassette control section 92 that controls the overall operation of the electronic cassette 32. The cassette control section 92 is structured to include a microcomputer, and has a CPU (Central Processing Unit) 92A, a memory 92B including a ROM (Read Only Memory) and a RAM (Random Access Memory), and a non-volatile storage 92C formed from an HDD (Hard Disk Drive), a flash memory, or the like.

On the other hand, the plural light-emitting elements 166 are provided at the light-emitting panel 61 in correspondence with the respective light-emitting portions 162. Plural wires 172, which are individually connected to the light-emitting elements 166 respectively, are provided at the light-emitting panel 61. The respective wires 172 are connected to the cassette control section 92. Accordingly, the cassette control section 92 can control the light emission of the respective light-emitting elements 166.

Further, a wireless communication section 94 is connected to the cassette control section 92. The wireless communication section 94 relating to the present exemplary embodiment corresponds to wireless LAN (Local Area Network) standards such as IEEE (Institute of Electrical and Electronics Engineers) 802.11a/b/g/n or the like, and controls the transfer of various types of information to and from external devices by wireless communication. The cassette control section 92 can communicate wirelessly with the console 42 via the wireless communication section 94, such that the transmission and reception of various types of information to and from the console 42 is possible.

A power source section 96 is provided at the electronic cassette 32. The above-described various types of circuits and respective elements (the gate line driver 80, the signal processing section 82, the image memory 90, the wireless communication section 94, the cassette control section 92, the light-emitting elements 166, and the like) are operated by electric power supplied from the power source section 96. The power source section 96 incorporates therein the aforementioned battery (secondary battery) 96A so that the portability of the electronic cassette 32 is not impaired, and supplies electric power from the charged battery 96A to the various types of circuits and respective elements. Note that, in FIG. 12, illustration of the wires that connect the power source section 96 with the various types of circuits and respective elements is omitted.

Figure 13:
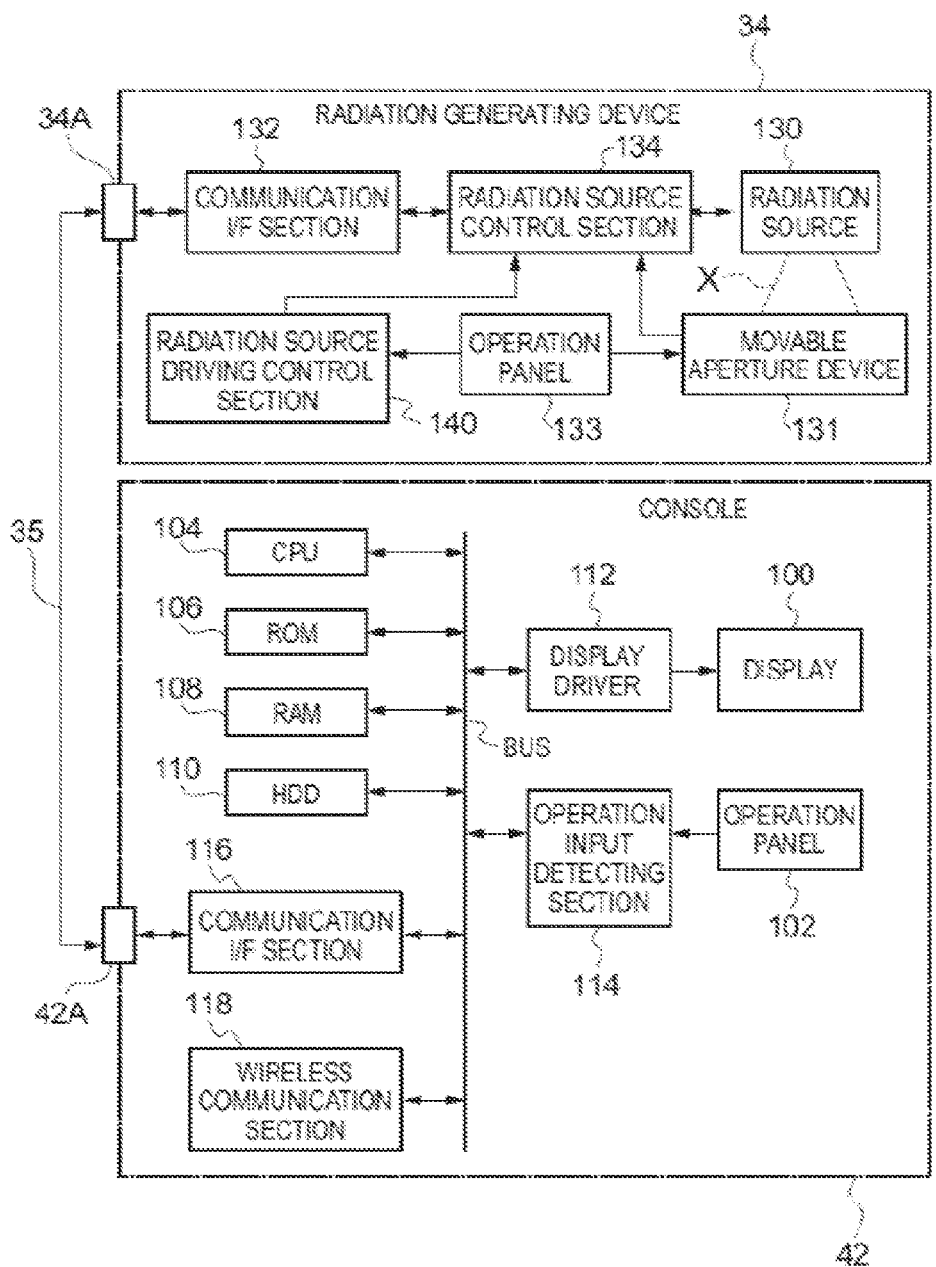
FIG. 13 is a block diagram showing the structure of main portions of the electrical systems of a console and a radiation generating device relating to the exemplary embodiments.

A block diagram showing the structures of main portions of the electrical systems of the console 42 and the radiation generating device 34 relating to the present exemplary embodiment is shown in FIG. 13.

The console 42 is structured as a server computer, and has a display 100 that displays an operation menu, captured radiographic images and the like, and an operation panel 102 that is structured to include plural keys and at which various types of information and operating instructions are inputted.

The console 42 relating to the present exemplary embodiment includes a CPU 104 that governs the operations of the overall device, a ROM 106 in which various types of programs, including control programs, and the like are stored in advance, a RAM 108 that temporarily stores various types of data, an HDD 110 that stores and holds various types of data, a display driver 112 that controls the display of various types of information on the display 100, and an operation input detecting section 114 that detects the operated state of the operation panel 102. Further, the console 42 has a communication interface (I/F) section 116 that, via a connection terminal 42A and a communication cable 35, carries out transmission and reception of various types of information, such as exposure conditions that will be described later and the like, with the radiation generating device 34, and a wireless communication section 118 that carries out transmission and reception of various types of information, such as imaging conditions and image data and the like, with the electronic cassette 32 by wireless communication.

The CPU 104, the ROM 106, the RAM 108, the HDD 110, the display driver 112, the operation input detecting section 114, the communication interface section 116, and the wireless communication section 118 are connected to one another via a system bus BUS. Accordingly, the CPU 104 can access the ROM 106, the RAM 108 and the HDD 110, and can respectively carry out control of display of various types of information on the display 100 via the display driver 112, control of transmission and reception of various types of information with the radiation generating device 34 via the communication I/F section 116, and control of transmission and reception of various types of information with the radiation generating device 34 via the wireless communication section 118. Further, the CPU 104 can, via the operation input detecting section 114, grasp the operated state of the operation panel 102 by a user.

On the other hand, the radiation generating device 34 has the radiation source 130 that emits the radiation X, a movable aperture device 131 that limits the irradiation region of the radiation X emitted by the radiation source 130, a communication I/F section 132 that transmits and receives various types of information such as exposure conditions and the like to and from the console 42, a radiation source control section 134 that controls the radiation source 130 on the basis of received exposure conditions, and a radiation source driving control section 140 that, by controlling the supply of electric power to respective driving sources provided at the supporting/moving mechanism 52, controls movement of the radiation source 130 in the vertical direction.

The radiation source control section 134 also is structured to include a microcomputer, and stores the received exposure conditions and posture information. The exposure conditions received from the console 42 include information such as the tube voltage, the tube current, the irradiation time period, and the like. When starting of exposure is instructed, the radiation source control section 134 causes the radiation X to be irradiated from the radiation source 130 on the basis of the received exposure conditions. The radiation X that is irradiated from the radiation source 130 passes through the movable aperture device 131 and is irradiated onto the patient.

Figure 14:
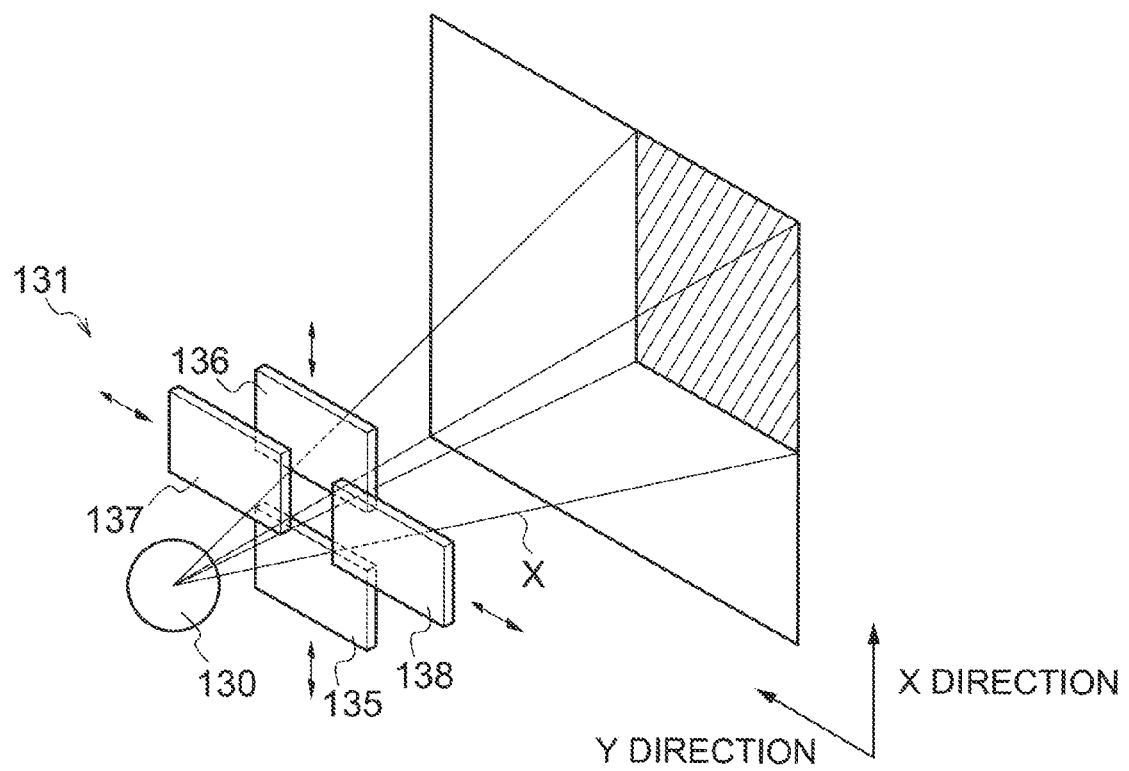
FIG. 14 is a perspective view showing the structure of a movable aperture device relating to the exemplary embodiments.

As shown in FIG. 14, slit plates 135, 136, and slit plates 137, 138 are provided at the movable aperture device 131. The slit plates 135, 136 and the slit plates 137, 138 can be moved by the driving force of an unillustrated motor or solenoid. Due to the slit plates 135, 136 individually moving in one direction (the X direction), the movable aperture device 131 changes, in the X direction, the irradiation region of the radiation X by the radiation source 130. Due to the slit plates 137, 138 individually moving in a direction (the Y direction) intersecting the one direction, the movable aperture device 131 changes, in the Y direction, the irradiation region of the radiation X by the radiation source 130.

An operation panel 133, for operating the slit plates 135, 136 and the slit plates 137, 138 and for operating the supporting/moving mechanism 52, is provided at the radiation generating device 34. The irradiation region of the radiation X can be changed by an operator operating the operation panel 133 and adjusting the position of the radiation source 130 by the supporting/moving mechanism 52 and the arranged relationship of the slit plates 135, 136 and the slit plates 137, 138. Note that the operator may be made to confirm the irradiation region of the radiation X by, for example, providing an image pick-up camera in a vicinity of the radiation source 130, and picking-up the part to be imaged that is to be imaged by the radiation, and displaying the part to be imaged on the display 100 of the console 42. Further, the operator may be made to confirm the irradiation region of the radiation X by providing a visible light lamp, that illuminates visible light, in a vicinity of the radiation source 130, and causing the part to be imaged of the body of the subject to be illuminated.

Operation of the imaging system 18 relating to the present exemplary embodiment is described next.

In the imaging system 18 relating to the present exemplary embodiment, still imaging that carries out imaging one at a time, and through imaging that carries out imaging continuously, are possible, and still imaging or through imaging can be selected as the imaging mode.

When capturing of a radiographic image is to be carried out, the terminal device 12 (see FIG. 1) receives an imaging request from a doctor or a radiology technician. The patient who is the object of imaging, the part to be imaged that is the object of imaging, and the imaging mode are designated in this imaging request. The tube voltage, the tube current, the irradiation time period and the like are designated as needed in the imaging request.

The terminal device 12 informs the RIS server 14 of the contents of the received imaging request. The RIS server 14 stores, in the database 14A, the contents of the imaging request notified from the terminal device 12.

By accessing the RIS server 14, the console 42 acquires the contents of the imaging request and the attribute information of the patient who is the object of imaging from the RIS server 14, and displays the contents of the imaging request and the attribute information of the patient on the display 100 (see FIG. 13).

The operator starts capturing of radiographic images on the basis of the contents of the imaging request displayed on the display 100.

When capturing of a radiographic image is instructed, the console 42 displays, on the display 100, an unillustrated imaging menu input screen for input of the imaging conditions and the like, and requests that the operator input information therein. A message, that urges the operator to input information into the imaging menu as the imaging conditions for the radiographic image capturing that is to be carried out from now on, and input regions for the various types of information, are displayed in the imaging menu input screen. The imaging menu includes, for example, the name of the subject on whom radiographic image capturing is to be carried out, the part to be imaged, the posture at the time of imaging (in the present exemplary embodiment, supine or standing), the exposure conditions of the radiation X at the time of imaging (in the present exemplary embodiment, the tube voltage, the tube current and the irradiation time period at the time of exposure of the radiation X), the imaging mode, the frame rate, and the like.

For example, as shown in FIG. 2, when carrying out imaging of a portion to be treated of a patient who is lying on the supine position stand 46, the operator places the electronic cassette 32 in the holding portion 152 of the supine position stand 46. Further, the operator operates the operation panel 133 and places the radiation generating device 34 above the part to be imaged, and operates the operation panel 133 and limits the irradiation region of the radiation X by the movable aperture device 131 such that the radiation X is irradiated only on the part to be imaged and the periphery thereof. When the operation panel 133 is operated and the radiation source driving control section 140 and the movable aperture device 131 operate, the radiation source control section 134, on the basis of the operated states of the radiation source driving control section 140 and the movable aperture device 131, specifies the irradiation region at which the radiation X is to be irradiated from the radiation source 130 with respect to the supine position stand 46, and informs the console 42 of the specified irradiation region.

Further, at the operation panel 102, the operator designates still imaging or through imaging as the imaging mode. In a case in which the operator designates still imaging, the operator designates, at the operation panel 102, the tube voltage, the tube current, the irradiation time period and the like for the time when the radiation X is to be irradiated. In a case in which the operator designates through imaging, the operator designates, at the operation panel 102, the tube voltage, the tube current, and the frame rate of the through imaging for the time when the radiation X is to be irradiated.

When still imaging is designated as the imaging mode, the console 42 transmits various information such as the tube voltage, the tube current, the irradiation time period, and the like to the radiation generating device 34 as the exposure conditions. When through imaging is designated as the imaging mode, the console 42 transmits various information such as the tube voltage, the tube current and the like to the radiation generating device 34 as the exposure conditions. Further, when still imaging is designated as the imaging mode, the console 42 transmits various types of information, such as the imaging mode, the exposure conditions, the irradiation region notified from the radiation generating device 34, and the like, to the electronic cassette 32 as the imaging conditions. When through imaging is designated as the imaging mode, the console 42 transmits various types of information, such as the imaging mode, the exposure conditions, the irradiation region notified from the radiation generating device 34, the frame rate of the through imaging, and the like, to the electronic cassette 32 as the imaging conditions.

When the radiation source control section 134 of the radiation generating device 34 receives the exposure conditions from the console 42, the radiation source control section 134 stores the received exposure conditions. When the cassette control section 92 of the electronic cassette 32 receives the imaging conditions from the console 42, the cassette control section 92 stores the received imaging conditions in the storage 92C.

When preparations for imaging are completed, the operator carries out, with respect to the operation panel 102 of the console 42, an instructing operation that instructs the start of imaging.

When an instructing operation that instructs the start of imaging is carried out with respect to the operation panel 102, the console 42 transmits instruction information that instructs the start of exposure to the radiation generating device 34 and the electronic cassette 32.

When the radiation generating device 34 receives instruction information that instructs the start of exposure, the radiation generating device 34 starts generating and emitting radiation at the tube voltage and the tube current that correspond to the exposure conditions received from the console 42.

When the cassette control section 92 of the electronic cassette 32 receives instruction information that instructs the start of exposure, the cassette control section 92 carries out imaging control in accordance with the imaging mode that is stored as an imaging condition in the storage 92C.

Concretely, when the imaging mode is the still imaging mode, after the irradiation time period, that was designated by the exposure conditions included in the imaging conditions, elapses, the cassette control section 92 controls the gate line driver 80 such that on signals are outputted from the gate line driver 80 to the respective gate lines 76 in order and line-by-line.

On the other hand, when the imaging mode is the through imaging mode, the cassette control section 92 determines an image-capturing cycle that corresponds to the frame rate designated in the exposure conditions included in the imaging conditions, and, at each image-capturing cycle, controls the gate line driver 80 such that on signals are outputted from the gate line driver 80 to the respective gate lines 76 in order and line-by-line.

At the TFT substrate 66, when the respective TFTs 70 that are connected to the respective gate lines 76 are turned on in order and line-by-line, the charges that are accumulated in the respective storage capacitors 68 flow-out in order and line-by-line to the respective data lines 78 as electric signals. The electric signals, which have flowed-out to the respective data lines 78, are converted into digital image data at the signal processing section 82, and are stored in the image memory 90.

The cassette control section 92 transmits at all times the image information stored in the image memory 90 to the console 42 by wireless communication.

In the case of through imaging, when imaging is to be finished, the operator carries out an instructing operation that instructs ending of imaging, with respect to the operation panel 102 of the console 42.

When an instructing operation that instructs ending of imaging is carried out with respect to the operation panel 102, the console 42 transmits instruction information that instructs ending of exposure to the radiation generating device 34 and the electronic cassette 32. Due thereto, the radiation generating device 34 stops irradiating radiation, and the electronic cassette 32 ends the through imaging.

At the radiation detector 60, there are cases in which some of the charges are trapped in the impurity potentials within the sensor portions 72. If the amount of radiation that is irradiated is great, the signal levels of lag signals that are due to charges being trapped in the impurity potentials become high. Therefore, when carrying out imaging by irradiating a large amount of radiation, a step arises in the signal levels of the lag signals at the portion where radiation that has passed through the subject is irradiated, and the portion where radiation has not passed through the subject and is irradiated as is (hereinafter called directly irradiated portion).

Further, many lag signals are generated immediately after imaging, but decrease along with the passage of time and quickly disappear.

Thus, in the present exemplary embodiment, when through imaging is designated as an imaging condition, in conformance with the image-capturing cycle, light calibration processing is carried out in which the respective light-emitting portions 162 of the light-emitting panel 61 are made to emit light, the lights are illuminated onto the sensor portions 72 of the respective pixels 74 of the radiation detector 60, and the impurity potentials of the respective sensor portions 72 are filled-in.

Figure 15:
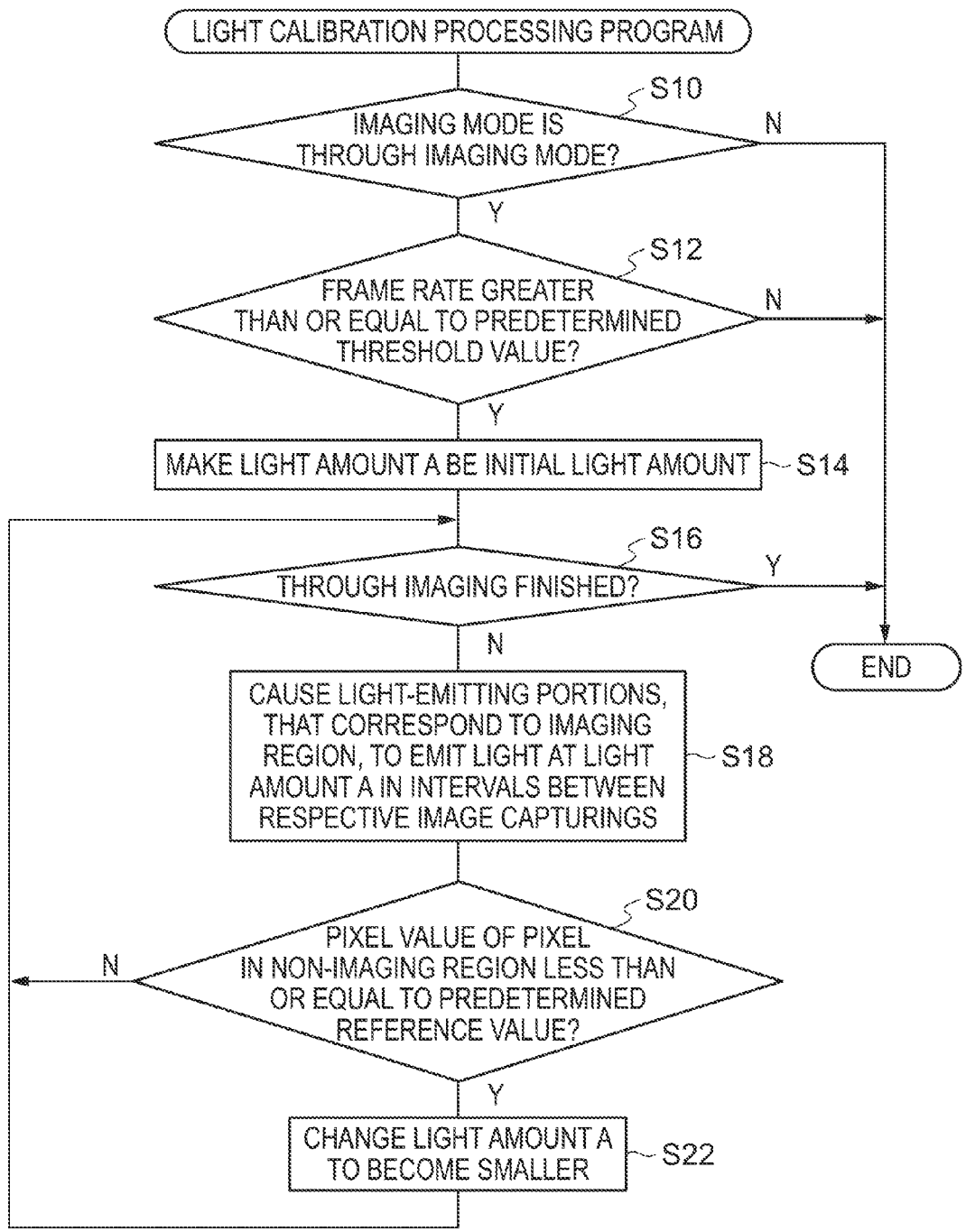
FIG. 15 is a flowchart showing the flow of processings of a light calibration processing program relating to a first exemplary embodiment.

FIG. 15 is a flowchart showing the flow of processings of a light calibration processing program that is executed by the CPU 92A of the cassette control section 92 at the time when instruction information that instructs the start of exposure is received. Note that this program is stored in advance in a predetermined area of the memory 92B (ROM).

In step S10 of FIG. 15, it is judged whether or not the imaging mode expressed by the imaging conditions is the through imaging mode. If the judgment is affirmative, the routine moves on to step S12, whereas if the judgment is negative (the imaging mode is the still imaging mode), processing ends.

In step S12, it is judged whether or not the frame rate expressed by the imaging conditions is greater than or equal to a predetermined threshold value. If the judgment is affirmative, the routine moves on to step S14. If the judgment is negative (the imaging mode is the still imaging mode), processing ends.

Here, the charges that are trapped in the impurity potentials within the respective sensor portions 72 of the radiation detector 60 are released frequently during the several msec to several tens of msec after imaging, and, when around several hundred msec elapses after imaging, the charges drop to a level that does not affect images. Therefore, if the frame rate of the through imaging is high, many lag signals are included in the electric signals that have flowed-out to the respective data lines 78, and residual images are generated in the images of the respective frames. Further, there is dispersion in the amounts of the lag signals among the respective frames, and there is dispersion in the residual images the are generated in the images of the respective frames.

Therefore, in the present exemplary embodiment, light calibration is carried out when the frame rate of through imaging that is designated as an imaging condition is greater than or equal to a predetermined threshold value (e.g., 30 fps) at which residual images are generated due to charges trapped in the impurity potentials within the respective sensor portions 72 of the radiation detector 60. In this light calibration, in the intervals between the image capturings of the respective frames, light is illuminated onto the radiation detector 60 and the impurity potentials within the respective sensor portions 72 are filled-in with charges. Due thereto, the charge amounts trapped in the impurity potentials in the respective sensor portions 72 become large and the amount of the lag signals included in the electric signals that flow-out to the respective data lines 78 becomes large, but because the amounts of the lag signals that flow-out to the respective data lines 78 respectively become a substantially uniform amount, residual images due to the effects of previous image capturings can be eliminated. Further, by filling-in the impurity potentials within the respective sensor portions 72 in advance, dispersion in the lag signals that arise at the respective frames also can be suppressed.

In step S14, light amount A, that the respective light-emitting portions 162 of the light-emitting panel 61 are to be made to emit, is made to be a predetermined initial light amount. This initial light amount is set to a value at which the impurity potentials within the respective sensor portions 72 are sufficiently filled-in by charges, and there is little dispersion in the residual images that are generated at the radiation detector 60, and the residual image correction of the images can be kept to a simple level.

In step S16, it is judged whether or not through imaging is finished. When the judgment is affirmative, processing ends, whereas, when the judgment is negative, the routine moves on to step S18.

In step S18, the irradiation region that is included in the imaging conditions is made to be the imaging region, and, during the interval between each image capturing at each image-capturing cycle by the radiation detector 60, the light-emitting portions 162 corresponding to the imaging region, among the respective light-emitting portions 162 of the light-emitting panel 61, are made to emit light at light amount A.

At the radiation detector 60, synchronously with the image capturing, light is illuminated from the light-emitting panel 61 onto the sensor portions 72 of the respective pixels 74 corresponding to the imaging region.

Due thereto, the occurrence of residual images at the portions corresponding to the imaging region in the video images that are captured by through imaging is suppressed. Further, among the respective light-emitting portions 162 of the light-emitting panel 61, the light-emitting portions 162 that correspond to the imaging region are made to emit light. Therefore, electric power consumption can be suppressed as compared with a case in which light calibration is carried out by making all of the light-emitting portions 162 emit light.

Further, the higher the temperature of the radiation detector 60, the more that the lag signals, that are due to charges being trapped in the impurity potentials of the respective sensor portions 72 of the radiation detector 60, increase. Moreover, at the respective sensor portions 72 of the radiation detector 60, charges are also generated due to dark current, and, the higher the temperature, the more that the generated charge amount increases as well. These charges due to dark current are also generated at the sensor portions 72 of the pixels 74 at which radiation is not irradiated.

Thus, in step S20, it is judged whether or not, of the radiographic image that was captured most recently by the radiation detector 60, the pixel value of a pixel in a non-imaging region is less than or equal to a predetermined reference value. If the judgment is affirmative, the routine moves on to step S22, whereas, if the judgment is negative, the routine moves on to step S16. The pixel in the non-imaging region may be any of the pixels in the non-imaging region, and may be, for example, the pixel that is furthest away from the imaging region (if there are plural pixels that are farthest, any may be selected), or any pixel that is positioned at an end portion of the non-imaging region, or, plural candidate pixels may be set in advance and any pixel that is in the non-imaging region among these plural candidate pixels may be used, or any pixel of the non-imaging region may be appropriately selected. Further, instead of the pixel value of a pixel in the non-imaging region, it can be judged whether or not the average value of the pixel values of all pixels in the non-imaging region, or the average value of specific pixels in the non-imaging region, is less than or equal to the reference value.

In step S22, the value of the light amount A is changed slightly by a predetermined value, and the routine moves on to step S16.

The pixel values of the image of the non-imaging region of the radiographic image include pixel values due to dark current. Therefore, if a pixel value of the image of the non-imaging region of the radiographic image is less than or equal to the predetermined reference value, the temperature is low and the trapping in the impurity potentials of the sensor portions 72 also decreases. Therefore, the electric power that is consumed can be held down by lowering the light amount A that the respective light-emitting portions 162 of the light-emitting panel 61 are made to generate.

Note that the present exemplary embodiment describes a case in which the light amount A that is generated at the respective light-emitting portions 162 is lowered. However, the illumination time period may be changed so as to become shorter while the light amount that is generated at the respective light-emitting portions 162 is kept constant. Or, the light amount can be decreased and at the same time the illumination time period can be changed to be shorter.

As described above, in accordance with the present exemplary embodiment, the plural light-emitting portions 162 are provided that can individually illuminate light for deleting residual images per sectional region obtained by dividing the detection region 66A, at which the plural sensor portions 72 are formed, of the radiation detector 60 into plural sectional regions. When still imaging is designated as an imaging condition, illumination of light from the respective light-emitting portions 162 is not carried out. When through imaging is designated as an imaging condition and the frame rate of the through imaging is greater than or equal to a predetermined threshold value, light calibration is carried out by causing light to be illuminated from the respective light-emitting portions 162. Consumption of electric power can thereby be suppressed while the generation of residual images is suppressed.

Further, in accordance with the present exemplary embodiment, among the respective light-emitting portions 162 of the light-emitting panel 61, the light-emitting portions 162 that correspond to the imaging region are made to emit light. Therefore, consumption of electric power can be suppressed as compared with a case in which light calibration is carried out by causing all of the light-emitting portions 162 to emit light.

Moreover, in accordance with the present exemplary embodiment, the lower the charge amounts due to dark current generated at the respective sensor portions 72 of the non-imaging region of the radiation detector 60, the more the light amount that is illuminated from the light-emitting portions 162 is reduced. Consumption of electric power can thereby be suppressed.

[Second Exemplary Embodiment]

A second exemplary embodiment is described next.

The structures of the RIS 10, the imaging system 18, the electronic cassette 32, and the radiation detector 60 relating to the second exemplary embodiment are the same as those of the above-described first exemplary embodiment (see FIGS. 1-14), and therefore, description thereof is omitted here.

At the electronic cassette 32 relating to the present exemplary embodiment, still imaging can be carried out in the midst of through imaging.

At the console 42, during through imaging, an operation screen that enables instruction of the capturing of a still image is displayed on the display 100. The tube voltage, the tube current, the irradiation time period, and the like in the case of carrying out still imaging are inputted by the operator from the operation panel 102. The inputted tube voltage, tube current and irradiation time period are transmitted to the radiation generating device 34 and the electronic cassette 32 as exposure conditions for still imaging in the midst of through imaging. Upon receiving the exposure conditions for still imaging in the midst of through imaging from the console 42, the radiation source control section 134 of the radiation generating device 34 stores the received exposure conditions. Upon receiving the exposure conditions for still imaging in the midst of through imaging from the console 42, the cassette control section 92 of the electronic cassette 32 stores the received exposure conditions in the storage 92C.

When capturing of a still image is to be carried out in the midst of through imaging, the operator carries out, with respect to the operation panel 102 of the console 42, an instructing operation that instructs still imaging.

When, in the midst of through imaging, an instructing operation that instructs still imaging is carried out with respect to the operation panel 102, the console 42 transmits instruction information that instructs still imaging in the midst of through imaging to the radiation generating device 34 and the electronic cassette 32.

When the radiation generating device 34 receives instruction information that instructs still imaging in the midst of through imaging, the radiation generating device 34 starts generating and emitting radiation at the tube voltage and the tube current that correspond to the exposure conditions received from the console 42.

When the cassette control section 92 of the electronic cassette 32 receives instruction information that instructs still imaging in the midst of through imaging, after the passage of the irradiation time period that was specified by the exposure conditions for still imaging in the midst of through imaging that were stored in the storage 92C, the cassette control section 92 controls the gate line driver 80 such that on signals are outputted from the gate line driver 80 to the respective gate lines 76 in order and line-by-line, and reading-out of an image is carried out.

In still imaging, in order to obtain a highly detailed radiographic image, the radiation amount that is irradiated per unit time is large, and the radiation amount that is irradiated per unit time is about ten times to 100 times that of the case of through imaging. Therefore, when still imaging in the midst of through imaging is carried out, it is easy for residual images to arise in the radiographic images of the through imaging thereafter.

Further, even in still imaging in the midst of through imaging, it is preferable that there not be residual images in the radiographic image captured by the still imaging.

Thus, in the electronic cassette 32 relating to the present exemplary embodiment, when still imaging in the midst of through imaging is carried out, light calibration is carried out by causing all of the light-emitting portions 162 of the light-emitting panel 61 to respectively emit light, immediately before and immediately after the still imaging.

Figure 16:
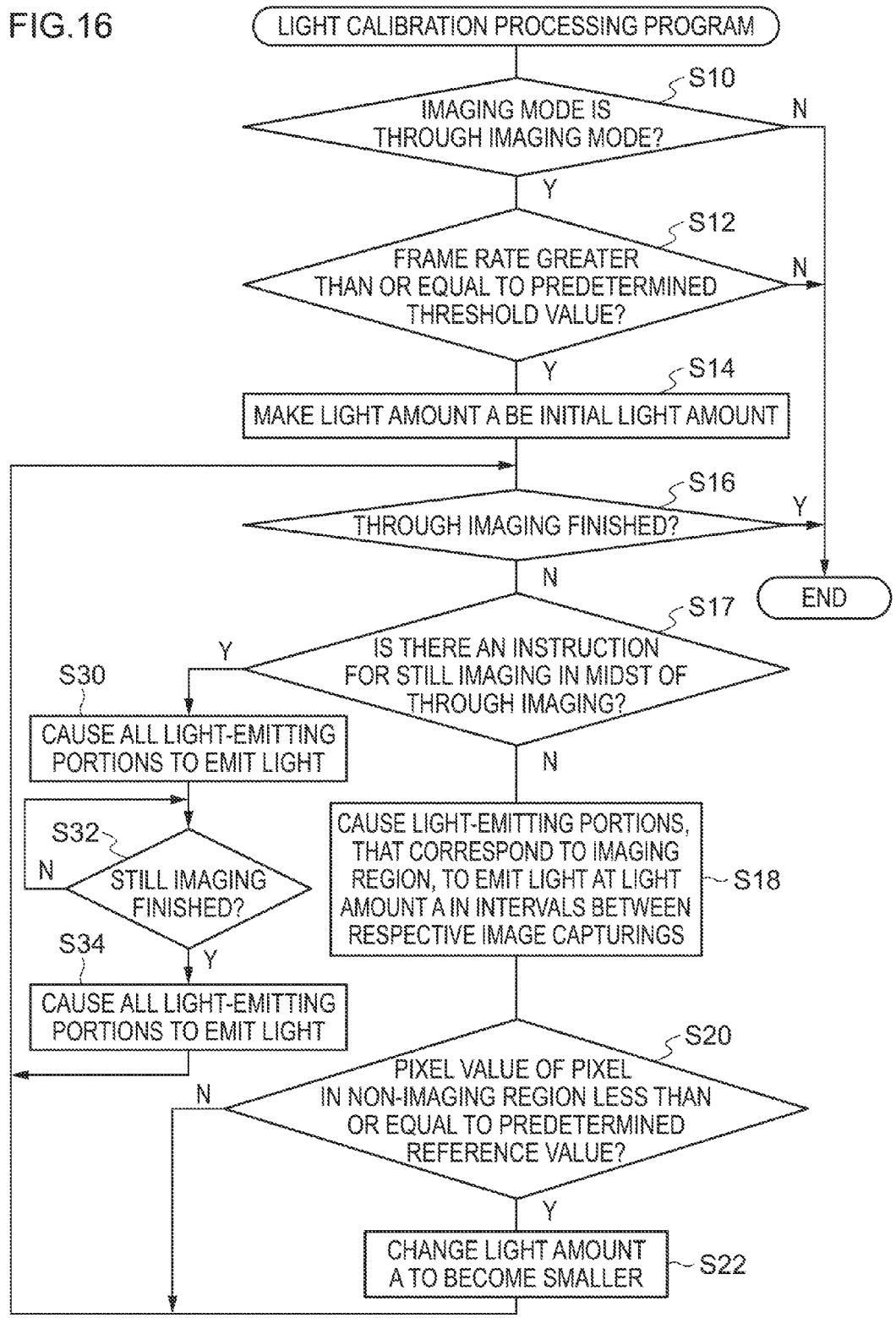
FIG. 16 is a flowchart showing the flow of processings of a light calibration processing program relating to a second exemplary embodiment.

FIG. 16 is a flowchart showing the flow of processings of a light calibration processing program relating to the second exemplary embodiment. Note that processings that are the same as those of the above-described first exemplary embodiment (see FIG. 15) are denoted by the same numerals, and description thereof is omitted here.

In step S17, it is judged whether or not instruction information that instructs still imaging in the midst of through imaging has been received. If the judgment is affirmative, the routine moves on to step S30, whereas, if the judgment is negative, the routine proceeds to step S18.

In step S30, all of the light-emitting portions 162 of the light-emitting panel 61 are made to emit light at a predetermined initial light amount.

In next step S32, it is judged whether or not the still imaging is finished. If the judgment is affirmative, the routine moves on to step S34. If the judgment is negative, the routine moves to step S32 again and awaits the end of the still imaging.

In next step S34, all of the light-emitting portions 162 of the light-emitting panel 61 are made to emit light at the predetermined initial light amount, and thereafter, the routine moves on to step S16.

In this way, when still imaging in the midst of through imaging is carried out, immediately before the still imaging, light calibration is carried out by causing all of the light-emitting portions 162 of the light-emitting panel 61 to emit light. Due thereto, residual images from the time of the through imaging arising in the image that is captured by the still imaging can be suppressed.

Further, when still imaging in the midst of through imaging is carried out, immediately after the still imaging, light calibration is carried out by causing all of the light-emitting portions 162 of the light-emitting panel 61 to emit light. Due thereto, even if a large amount of radiation is irradiated at the time of the still imaging, residual images arising in the through imaging thereafter can be suppressed.

Still further, by carrying out light calibration by causing all of the light-emitting portions 162 of the light-emitting panel 61 to respectively emit light immediately before and immediately after still imaging in this way, even if, for example, the sizes of the imaging regions are different in the still imaging and the through imaging, the effects of residual images of directly irradiated portions, at which the radiation is irradiated as is without passing through the subject, can be reduced.

As described above, in accordance with the present exemplary embodiment, when carrying out still imaging in the midst of through imaging that carries out imaging continuously, all of the light-emitting portions 162 are controlled to emit light immediately before the still imaging. Therefore, generation, in the image captured by the still imaging, of residual images from the through imaging can be suppressed.

Further, in accordance with the present exemplary embodiment, when carrying out still imaging in the midst of through imaging that carries out imaging continuously, all of the light-emitting portions 162 are controlled to emit light immediately after the still imaging. Therefore, generation, in the through imaging, of residual images from the still imaging can be suppressed.

The present invention is described above by using the first and second exemplary embodiments, but the technical scope of the present invention is not limited to the ranges described in the above respective exemplary embodiments. Various modifications and improvements can be added to the above-described exemplary embodiments within a range that does not deviate from the gist of the present invention, and forms to which such modifications or improvements have been added are also encompassed in the technical scope of the present invention.

Further, the above-described exemplary embodiments do not limit the inventions relating to the claims, nor is it the case that all of the combinations of features described in the exemplary embodiments are essential to the means of the present invention for solving the problems of the conventional art. Inventions of various stages are included in the above exemplary embodiments, and various inventions can be extracted from appropriate combinations of plural constituent features that are disclosed. Even if some of the constituent features are omitted from all of the constituent features that are shown in the exemplary embodiments, such structures from which some constituent features are omitted can be extracted as inventions provided that the effects of the present invention are obtained thereby.

For example, the above respective exemplary embodiments describe cases in which the present invention is applied to the electronic cassette 32 that is a portable radiographic imaging device, but the present invention is not limited to the same and may be applied to a stationary radiographic imaging device.

Further, the above-described exemplary embodiments describe cases in which control of the light emission of the light-emitting panel 61 is carried out at the cassette control section 92 of the electronic cassette 32. However, the present invention is not limited to the same. For example, the electronic cassette 32 and the console 42 may be connected by a wire, and control of the light emission of the light-emitting panel 61 may be carried out at the console 42.

Moreover, the above-described exemplary embodiments describe cases in which the irradiation region of the radiation is limited by the movable aperture device 131 of the radiation generating device 34, and, due to the console 42 informing the electronic cassette 32 of that irradiation region as the imaging region, the electronic cassette 32 acquires position information of the imaging region. However, the present invention is not limited to the same. For example, the electronic cassette 32 may acquire position information of the imaging region by specifying the irradiation region on which radiation is irradiated, from a radiographic image that was captured in the initial stage of through imaging. The irradiation region may be specified by comparing pixel values of respective pixels of the radiographic image with a predetermined threshold value that expresses that radiation has been irradiated. Further, at the console 42, when the part to be imaged is designated as an imaging condition, pattern images expressing features of various types of parts to be imaged may be stored in advance in the storage 92C, and the cassette control section 92 may specify the region at which the part to be imaged is positioned by carrying out pattern matching between the captured radiographic image and the pattern image that corresponds to the designated part to be imaged, and may make the specified region be the imaging region. Moreover, when through imaging is designated, the operator may input, from the operation panel 102 of the console 42, an imaging region, at which the part to be imaged is disposed, of the image-capturing surface 56 of the electronic cassette 32.

At the electronic cassette 32, in a case in which the imaging region moves, the light-emitting portions 162 that are made to emit light of the light-emitting panel 61 may be changed in accordance with the movement of the imaging region. For example, in the case of IVR (Interventional Radiology) in which a catheter, to whose distal end various instruments are mounted, is inserted into the body of a patient, and the distal end of the catheter is made to reach a lesion while the state within the body of the patient is observed in real time by through imaging from radiographic images displayed on a monitor, and treatment is carried out by operating the catheter from outside the patient's body, the distal end of the catheter may be detected, and a predetermined range from the distal end of the catheter may be made to be the imaging region. Any of various methods can be used as the method of detecting the distal end of the catheter. Because the absorption rate of radiation by the guide wire of the catheter differs greatly from those of respective parts of a human body, in the radiographic image, the density of the image portion corresponding to the guide wire of the catheter distinctly differs from the densities of the other image portions. Accordingly, for example, the position of the distal end portion of the guide wire of the catheter in the radiographic image can be detected by carrying out image processing such as, for example, binarizing the radiographic image by a threshold value that enables discrimination between the image portion corresponding to the guide wire of the catheter and the other image portions, and line-thinning the image portion corresponding to the guide wire of the catheter in the radiographic image after the binarization, and recognizing the position of the end portion of the curve obtained by the line-thinning to be the position of the distal end portion of the guide wire, or the like. Further, for example, an IC tag or magnetic body may be provided at the distal end portion of the catheter, and the distal end of the catheter may be detected by detecting the IC tag or the magnetic body by a sensor or the like.

Figure 17:
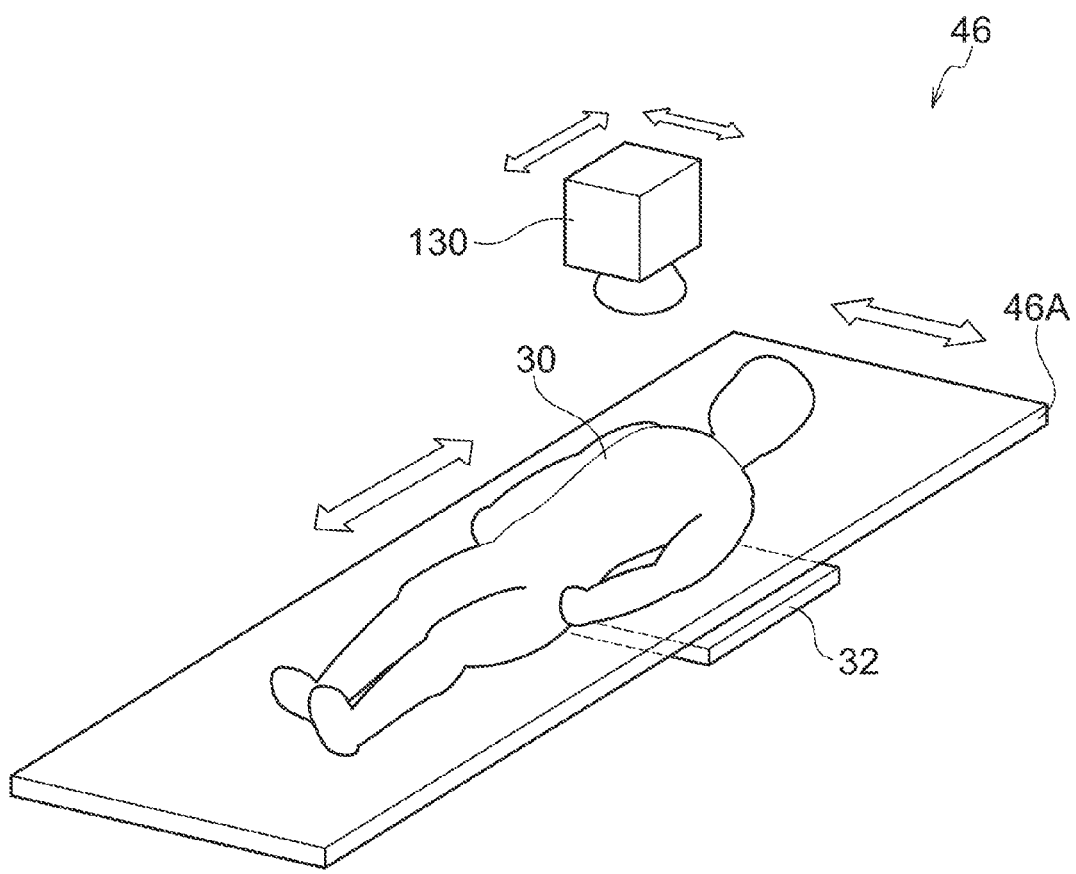
FIG. 17 is a perspective view schematically showing a supine position imaging stand that is structured such that a top plate is horizontally movable, relating to another exemplary embodiment.

Further, as shown in FIG. 17 for example, when a top plate 46A, on which the subject 30 lies, at the supine position stand 46 is structured so as to be movable horizontally, and the radiation source 130 and the top plate 46A are synchronously moved horizontally during through imaging such that the imaging region of the electronic cassette 32 is moved so as to not tend toward one specific portion, the light-emitting portions 162 that are made to emit light of the light-emitting panel 61 may be changed in accordance with the movement of the imaging region. By moving the imaging region of the electronic cassette 32 in this way, progression of deterioration at the one specific portion can be suppressed, and further, it is possible to suppress heat from increasing only at the one specific portion due to light from or driving of the light-emitting panel 61. Note that the imaging region may be moved continuously, or may be moved each time a predetermined amount of radiation is irradiated. Or, plural temperature sensors may be disposed at the detection region 66A and connected to the cassette control section 92, and temperatures of respective portions of the detection region 66A may be detected by the temperature sensors, and the imaging region may be moved when the temperature of the portion that has become the imaging region at the detection region 66A becomes a permitted value.

Figure 18A:
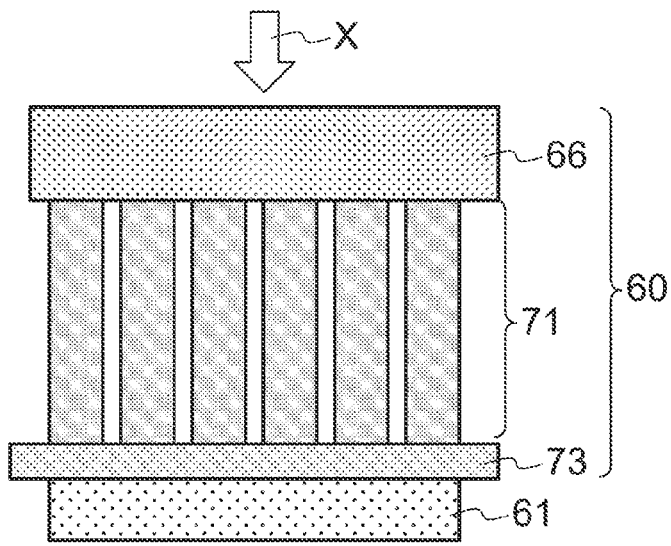
FIG. 18A is a sectional view showing the arranged structure of the radiation detector and the light-emitting panel relating to an exemplary embodiment.
Figure 18B:
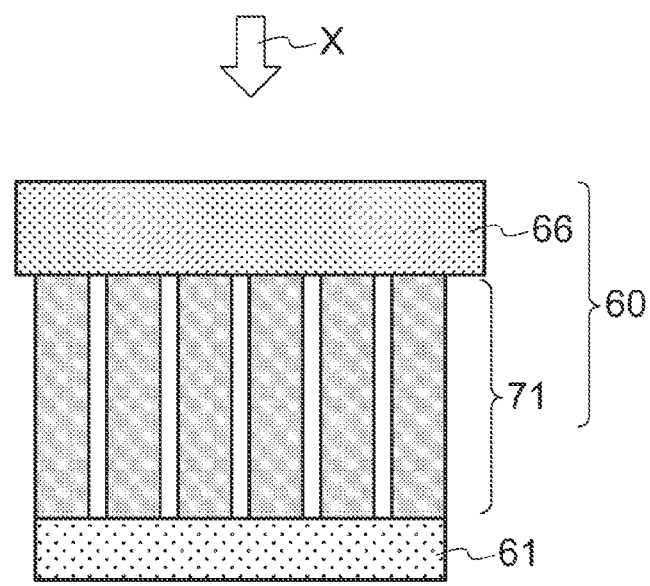
FIG. 18B is a sectional view showing the arranged structure of the radiation detector and the light-emitting panel relating to another exemplary embodiment.
Figure 19A:
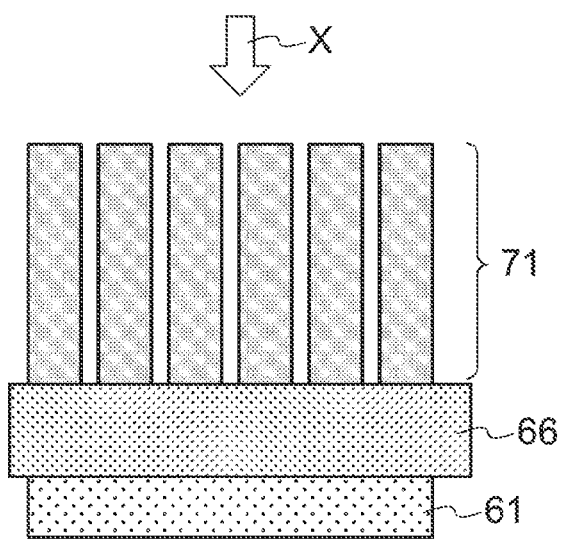
FIG. 19A and FIG. 19B are sectional views showing the arranged structure of the radiation detector and the light-emitting panel relating to yet another exemplary embodiment.
Figure 19B:
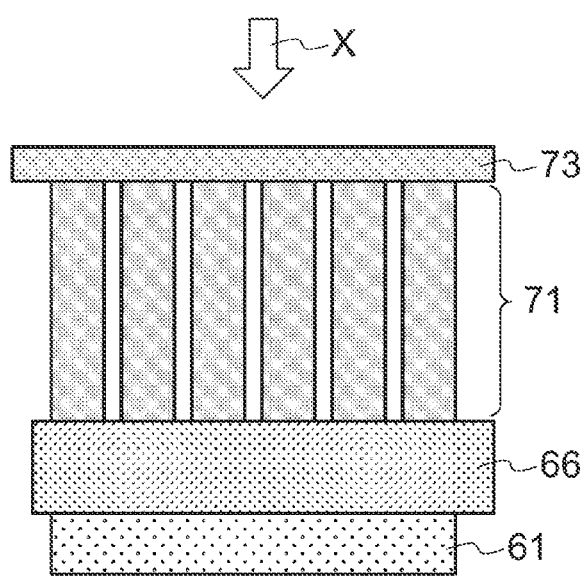
Figure 20A:
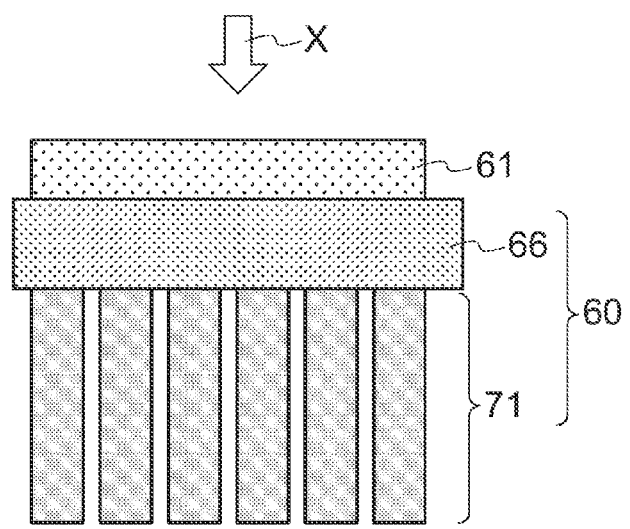
FIG. 20A and FIG. 20B are sectional views showing the arranged structure of the radiation detector and the light-emitting panel relating to still another exemplary embodiment.
Figure 20B:
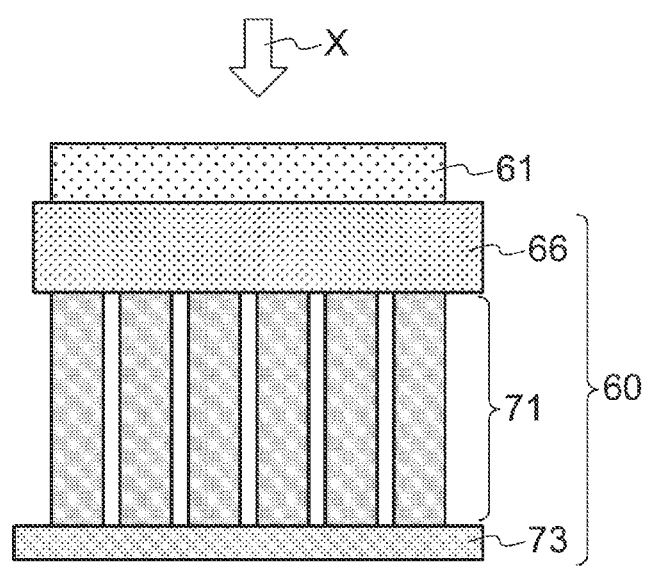

Further, the above respective exemplary embodiments describe cases in which, as shown in FIG. 18A, the scintillator 71 is made to be columnar crystals, the vapor deposition substrate 73 is made to be a substrate that is light-transmissive such as glass or the like, the light-emitting panel 61 is disposed at the vapor deposition substrate 73 side of the radiation detector 60, and the radiation detector 60 is disposed so as to be an obverse reading type in which the radiation X is incident from the TFT substrate 66 side. However, the present invention is not limited to the same. For example, as shown in FIG. 18B, without providing the vapor deposition substrate 73, the TFT substrate 66 may be made to be a vapor deposition substrate, columnar crystals (the scintillator 71) may be formed on the TFT substrate 66, and the radiation detector 60 may be disposed so as to be an obverse reading type in which the radiation X is incident from the TFT substrate 66 side. Or, as shown in FIG. 19A for example, without providing the vapor deposition substrate 73, the TFT substrate 66 may be made to be a vapor deposition substrate, columnar crystals (the scintillator 71) may be formed on the TFT substrate 66, the radiation detector 60 may be disposed so as to be to be a reverse reading type in which the radiation X is incident from the scintillator 71 side, the insulating substrate 64 that structures the TFT substrate 66 may be made to be a substrate that is light-transmissive, and the light-emitting panel 61 may be disposed on the surface, of the TFT substrate 66, at the side opposite the scintillator 71. Or, as shown in FIG. 19B for example, columnar crystals (the scintillator 71) may be formed on the vapor deposition substrate 73, the radiation detector 60 may be disposed so as to be a reverse reading type in which the radiation X is incident from the scintillator 71 side, the insulating substrate 64 that structures the TFT substrate 66 may be made to be a substrate that is light-transmissive, and the light-emitting panel 61 may be disposed at the surface, of the TFT substrate 66, at the side opposite the scintillator 71. Or, as shown in FIG. 20A for example, without providing the vapor deposition substrate 73, the TFT substrate 66 may be made to be a vapor deposition substrate, columnar crystals (the scintillator 71) may be formed on the TFT substrate 66, the radiation detector 60 may be disposed so as to be to be an obverse reading type in which the radiation X is incident from TFT substrate 66 side, the insulating substrate 64 that structures the TFT substrate 66 may be made to be a substrate that is light-transmissive, and the light-emitting panel 61 may be disposed on the surface, of the TFT substrate 66, at the side opposite the scintillator 71. Or, as shown in FIG. 20B for example, columnar crystals (the scintillator 71) may be formed on the vapor deposition substrate 73, the radiation detector 60 may be disposed so as to be to be an obverse reading type in which the radiation X is incident from the TFT substrate 66 side, the insulating substrate 64 that structures the TFT substrate 66 may be made to be a substrate that is light-transmissive, and the light-emitting panel 61 may be disposed on the surface, of the TFT substrate 66, at the side opposite the scintillator 71.

Figure 21:
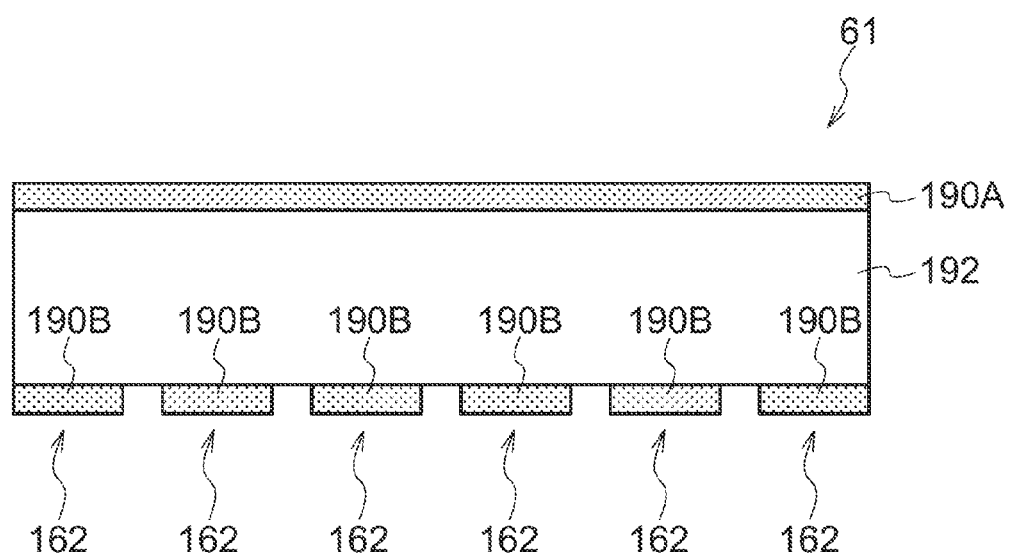
FIG. 21 is a sectional view showing a case in which the light-emitting portions of the light-emitting panel are structured by organic EL elements.

Further, although the exemplary embodiments describe cases in which the light-emitting panel 61 is structured by providing the light guiding plate 164, that is flat-plate shaped and rectangular, and the light-emitting element 166 per each of the light-emitting portions 162, the present invention is not limited to the same. For example, the respective light-emitting portions 162 may be structured by respective light-emitting elements such as organic EL (Electro Luminescent) elements or the like. An organic EL element is formed by organic matter 192 being sandwiched between two electrodes 190A, 190B. However, as shown in FIG. 21, one of the electrodes (the electrode 190A in FIG. 21) among the two electrodes 190A, 190B that structure the organic EL element may be used in common for the entire light-emitting panel 61, and the other electrode (the electrode 190B in FIG. 21) may be formed per light-emitting portion 162.

Although the above exemplary embodiments describe cases in which only the light-emitting portions 162 that correspond to the imaging region are made to emit light, the present invention is not limited to the same. For example, the light-emitting portions 162 that correspond to the imaging region may be made to emit light at a predetermined light amount (e.g., light amount A), and at least some of the light-emitting portions 162 corresponding to the non-imaging region may be made to emit light of a lower light amount than the light-emitting portions 162 corresponding to the imaging region. For example, at the three light-emitting portions 162 (162A through 162C) that are shown in FIG. 9, when the light-emitting portion 162B corresponds to the imaging region, the light-emitting portion 162B may be made to emit light at a predetermined light amount, and the light-emitting portion 162A and the light-emitting portion 162C may be made to emit light at a light amount that is 5% of the predetermined light amount. When plural light-emitting portions 162 of the non-imaging region are made to emit light, the light amounts thereof may be decreased more the further away that the light-emitting portion 162 is from the imaging region. Due thereto, the occurrence of a difference in image quality due to residual images at the portions corresponding to the imaging region and the non-imaging region of the radiographic image can be suppressed.

The above exemplary embodiments describe cases in which the absence/presence of illumination of, the light amount of, and the illumination time period of light from the respective light-emitting portions 162 of the light-emitting panel 61 are controlled in accordance with the imaging conditions, but the present invention is not limited to the same. For example, imaging actual results information that expresses actual results of imaging of radiographic images in the past may be stored in the storage 92C, and the cassette control section 92 may control the absence/presence of illumination of, the light amount of, and the illumination time period of light from the respective light-emitting portions 162 of the light-emitting panel 61 in accordance with actual results of imaging that are expressed by the imaging actual results information that is stored in the storage 92C.

The actual results of imaging may be, for example, the position of a directly irradiated portion, within the detection region 66A, at which radiation has been irradiated as is without passing through the subject. From the pixel values of the respective pixels of a captured radiographic image, the cassette control section 92 discriminates a directly irradiated portion, within the detection region 66A, at which radiation has been irradiated as is without passing through the subject, and stores the position of the directly irradiated portion and the imaging time period in the storage 92C. Then, when imaging is carried out, on the basis of the imaging actual results information that is stored in the storage 92C, the cassette control section 92 may cause the respective light-emitting portions 162 of the light-emitting panel 61 to emit light such that the light amount or the illumination time period is greater for the directly irradiated portion. Due thereto, consumption of electric power can be suppressed while the occurrence of residual images is suppressed, as compared with a case in which all of the light-emitting portions 162 of the light-emitting panel 61 are made to emit light.

Further, the actual results of imaging may be, for example, the temperature of the radiation detector 60 at the time of imaging. At the radiation detector 60, when the change in temperature between the image capturing at this time and the image capturing of the previous time is great (e.g., the image capturing of the previous time was imaging in a cold place or the like), there are cases in which there are effects on residual images that arise in the image capturing of this time. Therefore, for example, when there is a change in temperature of greater than or equal to a predetermined temperature from the image capturing of the previous time, the cassette control section 92 may carry out light calibration of the radiation detector 60 by causing all of the light-emitting portions 162 of the light-emitting panel 61 to emit light.

The actual results of imaging may be, for example, the actual results of the time immediately before or the actual results of image capturings of a predetermined number of times immediately before, or may be the actual results of all of the image capturings that have been carried out on that day of imaging. When the actual results of imaging of plural times of image capturing are stored, they may be weighted such that, the nearer the imaging time is to the current time, the greater the weight applied to the actual results of that image capturing.

Control corresponding to actual results of imaging and imaging conditions may be carried out in combination. For example, the respective light-emitting portions 162 of the light-emitting panel 61 may be made to emit light such that, within the imaging region as well, the light amount or the illumination time period for a directly irradiated portion is made to be large.

Figure 22A:
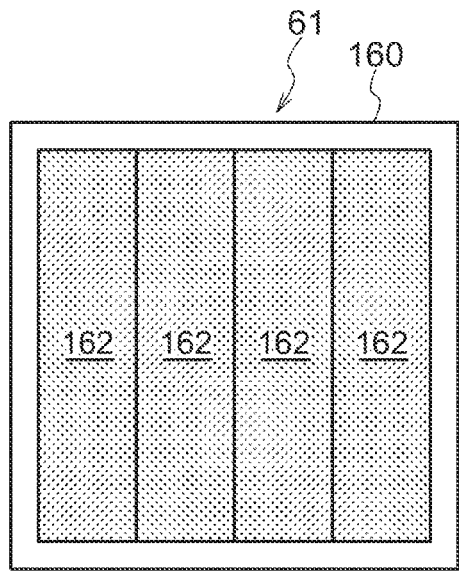
FIG. 22A through FIG. 22D are plan views showing the arranged structure of the light-emitting portions of the light-emitting panel relating to another exemplary embodiment.
Figure 22B:
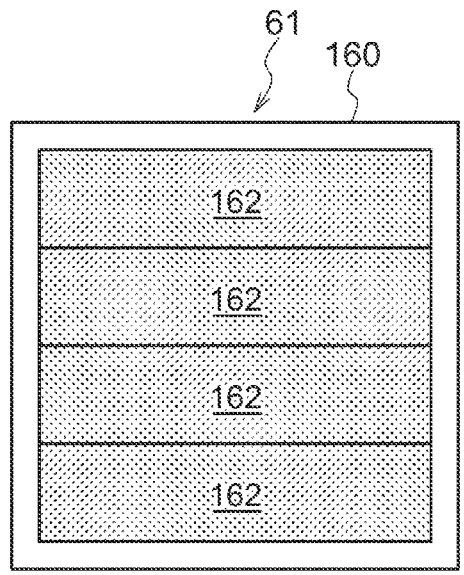
Figure 22C:
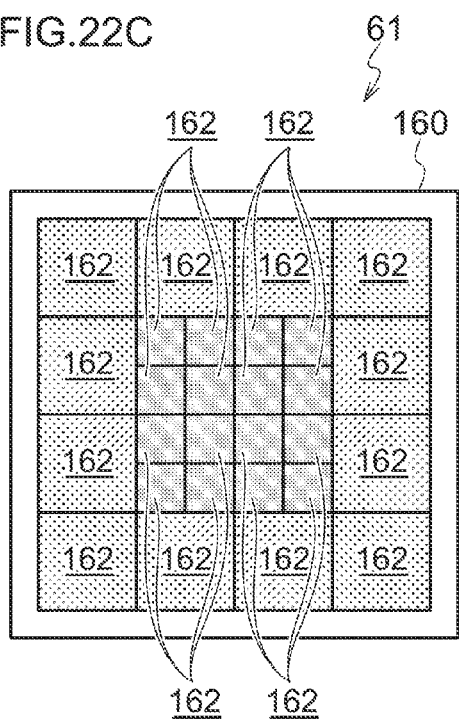

Further, the respective exemplary embodiments describe cases in which the light-emitting portions 162 of the light-emitting panel 61 are disposed in the form of a matrix as shown in FIG. 10, but the present invention is not limited to the same. For example, as shown in FIG. 22A and FIG. 22B, the plural light-emitting portions 162 may be provided in strip-like forms in a given direction (the row direction in FIG. 21) or in a direction (the column direction in FIG. 21) intersecting the given direction. By providing the light-emitting portions 162 in this way, even when the imaging region is moved, the control for changing the light-emitting portions 162, which are made to emit light, interlockingly with the movement of the imaging region becomes easy. Further, as shown in FIG. 22C for example, the plural light-emitting portions 162 may be provided by dividing the central portion of the light-emitting area of the light-emitting panel 61 more finely than the peripheral portion thereof. It is often the case that capturing of a radiographic image is carried out with the part to be imaged being disposed at the central portion of the image-capturing surface 56 of the electronic cassette 32.

Figure 22D:
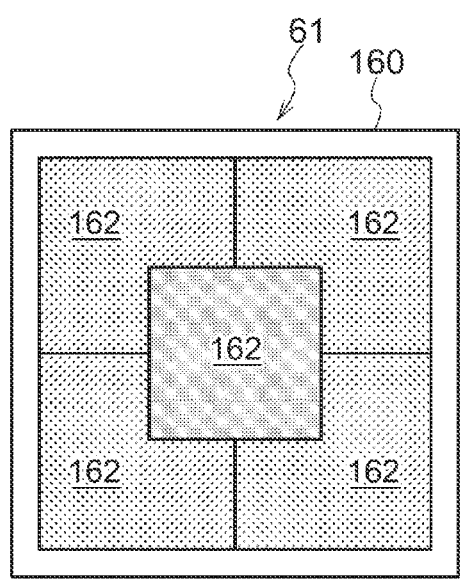

Therefore, by dividing the central portion of the light-emitting area of the light-emitting panel 62 more finely than the peripheral portion, the light-emitting portions 162 that are made to emit light can be controlled finely in accordance with the size of the part to be imaged, and therefore, consumption of electric power can be suppressed. Further, as shown in FIG. 22D for example, the light-emitting portions 162 may be provided by being distributed between the central portion and the peripheral portion of the light-emitting area of the light-emitting panel 61. In FIG. 22D, the plural light-emitting portions 162 are provided at the peripheral portion of the light-emitting area so as to each include a corner portion, but the present invention is not limited to the same. By providing the light-emitting portions 162 so as to be distributed among the central portion and the peripheral portion in this way, control of the light-emitting portions 162 that are made to emit light is easy.

The above exemplary embodiments describe cases in which charge amounts due to dark current that is generated at the respective sensor portions 72 of the non-irradiation region of the radiation detector 60 are detected, and control is carried out such that, the lower the detected charge amount due to dark current, the lower the light amount A. However, the present invention is not limited to the same. For example, the cassette control section 92 may carry out detection of the battery 96A, and, when the remaining amount of electric power stored in the battery 96A is less than a predetermined allowed amount (e.g., less than 20% of the electric power that the battery 96A can store), control may be carried out such that any of stopping of illumination of, decreasing of the light amount of, or shortening of the illumination time period of the light for the light calibration is carried out. In this way, by carrying out any of stopping of illumination of, decreasing of the light amount of, or shortening of the illumination time period of the light when the remaining amount of electric power stored in the battery 96A becomes low, the electric power that is used in the light calibration is held down. Therefore, in the case of through imaging, imaging can be carried out for a longer time, and, in the case of still imaging, more images can be captured.

Further, the above second exemplary embodiment describes a case in which, when carrying out still imaging in the midst of through imaging that carries out imaging continuously, all of the light-emitting portions 162 are made to emit light immediately before and immediately after the still imaging. However, the present invention is not limited to the same. For example, all of the light-emitting portions 162 may be made to emit light only at either one of immediately before or immediately after the still imaging.

The exemplary embodiments describe cases in which the radiation detector 60 is an indirect-conversion-type radiation detector that once converts radiation into light at the scintillator 71, and converts the converted light into charges at a photoconductive layer 30, and accumulates the charges. However, the radiation detector may be a direct-conversion-type radiation detector that directly converts radiation into charges at sensor portions using amorphous selenium or the like and accumulates the charges.

Figure 23:
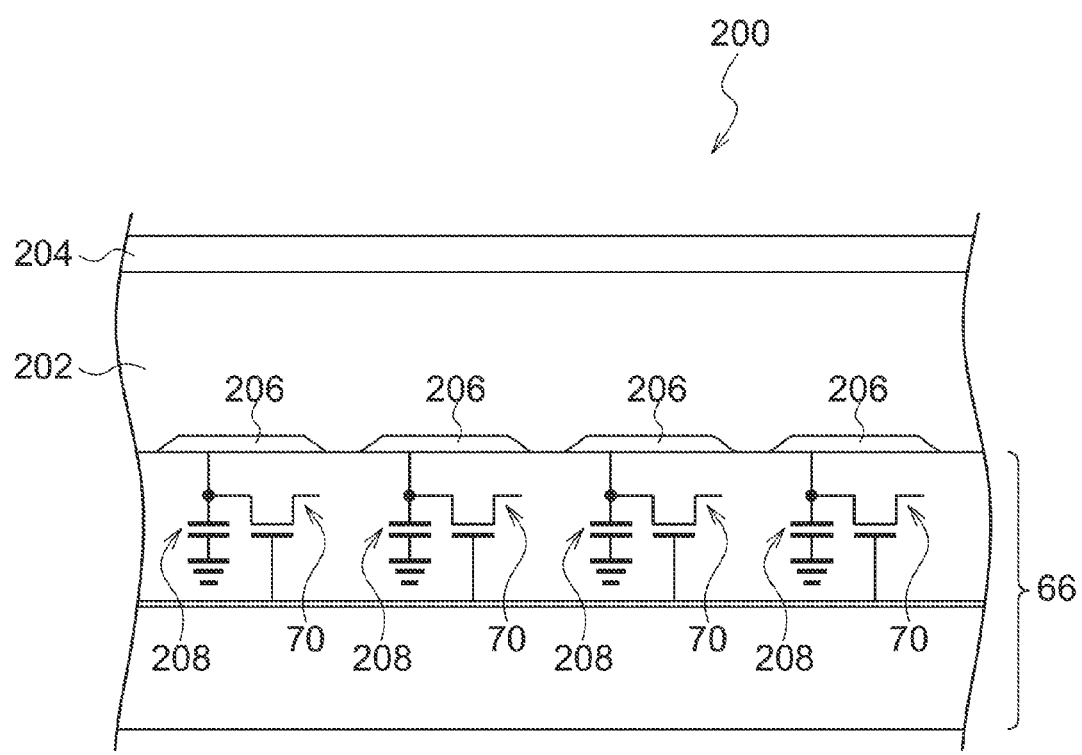
FIG. 23 is a sectional view schematically showing the structure of a direct-conversion-type radiation detector relating to another exemplary embodiment.

As shown in FIG. 23, in a direct-conversion-type radiation detector 200, a semiconductor layer 202 that converts incident radiation into charges is formed on the TFT substrate 66 as an example of a radiation converting layer that converts incident radiation.

A compound containing, as the main component thereof, at least one of amorphous Se, $Bi_{12}MO_{20}$ (M: Ti, Si, Ge), $Bi_4M_3O_{12}$ (M: Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs or the like, or the like, is used as the semiconductor layer 202. However, amorphous materials, that have high dark resistivity, exhibit good photoconductivity with respect to X-ray irradiation, and at which large surface area growth at low temperatures by vacuum deposition is possible, are preferable.

A bias electrode 204, that is formed on the obverse side of the semiconductor layer 202 and is for applying bias voltage to the semiconductor layer 202, is formed on the semiconductor layer 202.

In the direct-conversion-type radiation detector 200, in the same way as in the indirect-conversion-type radiation detector 60, the charge collecting electrodes 206 that collect the charges generated at the semiconductor layer 202 are formed at the TFT substrate 66.

Further, the TFT substrate 66 in the direct-conversion-type radiation detector 200 has charge storage capacitors 208 that accumulate the charges collected at the respective charge collecting electrodes 206. The charges that are accumulated in the respective charge storage capacitors 208 are read-out by the TFTs 70.

In this direct-conversion-type radiation detector 200 as well, there are cases in which charges become trapped in the impurity potentials within the semiconductor layer 202 and residual images arise, and there are cases in which light calibration is carried out. However, the consumption of electric power can be suppressed by applying the present invention.

Moreover, although the above respective exemplary embodiments describe cases in which the present invention is applied to the radiographic imaging device that captures radiographic images by detecting X-rays as radiation, the present invention is not limited to the same. The radiation that is the object of detection may be, other than X-rays, any of gamma rays, particle beams, or the like for example.

In addition, the structures that are described in the above exemplary embodiments are examples, and unnecessary portions may be deleted therefrom, new portions may be added thereto, and the states of connection and the like may be changed within a scope that does not deviate from the gist of the present invention.

Further, the flows of the processings of the various types of programs described in the above exemplary embodiments also are examples. Unnecessary steps thereof may be deleted therefrom, new steps may be added thereto, or the order of the processings thereof may be rearranged within a scope that does not deviate from the gist of the present invention.

What is claimed is:

1. A radiographic imaging device comprising:
an imaging panel at which a plurality of sensor portions, that detect radiation or light converted from radiation, are formed at a detection region, and that captures a radiographic image expressed by radiation or light converted from radiation, the detection region being divided into a plurality of sectional regions such that each sectional region is associated with more than one of the plurality of sensor portions;
a light illuminating section at which a plurality of light-emitting portions, that can individually illuminate light for erasing residual images, are provided per sectional region;
a storage section that stores imaging actual results information that expresses past actual results of imaging carried out by the imaging panel;
a control section that controls, per sectional region, the light-emitting portion associated with said sectional region such that, in accordance with at least one of actual results of imaging, that are expressed by the imaging actual results information stored in the storage section, and imaging conditions, controls absence/presence of illumination of, light amount of, and illumination time period of light from the light-emitting portion; and an acquisition section that acquires a position of an imaging region within the detection region; wherein the control section controls the light illuminating section so as to cause light to be illuminated from the light-emitting portions that correspond to the imaging region acquired by the acquisition section; and wherein the control section causes at least some of the light-emitting portions that correspond to a non-imaging region to emit light at a light amount lower than a light amount of the light-emitting portions that correspond to the imaging region.

2. The radiographic imaging device of claim 1, wherein the imaging conditions comprise information that designates which of still imaging, that carries out imaging one at a time, and through imaging, that carries out imaging continuously, is to be carried out, and when through imaging is designated as the imaging condition, the control section causes light to be illuminated from the respective light-emitting portions of the light illuminating section synchronously with imaging.

3. The radiographic imaging device of claim 1, wherein the imaging conditions comprise information designating a frame rate of through imaging, and when the frame rate of through imaging that is designated as the imaging condition is greater than or equal to a predetermined threshold value, the control section causes light to be illuminated from the respective light-emitting portions of the light illuminating section synchronously with imaging.

4. The radiographic imaging device of claim 1, wherein the imaging region is made to be an irradiation region at which radiation is irradiated onto the detection region.

5. The radiographic imaging device of claim 1, further comprising:

a detection section that detects a charge amount due to dark current that is generated at each sensor portion of a non-irradiation region of the imaging panel, wherein the control section controls the light illuminating section such that, the smaller the charge amount due to dark current that is detected by the detection section, the smaller the light amount and illumination time period.

6. The radiographic imaging device of claim 1, further comprising:

a battery that at least supplies electric power for driving the imaging panel and electric power for causing the respective light-emitting portions of the light illuminating section to emit light, wherein, when a remaining amount of electric power stored in the battery is less than a predetermined allowed amount, the control section controls the light illuminating section to carry out any of stopping of illumination of, decreasing of a light amount of, and shortening of an illumination time period of light.

7. The radiographic imaging device of claim 1, wherein when still imaging is to be carried out in the midst of through imaging that carries out imaging continuously, the control section controls the light illuminating section to cause all of the light-emitting portions to emit light at one or both of immediately before and immediately after the still imaging.

8. The radiographic imaging device of claim 1, wherein the actual results of imaging express a portion, within the detection region, at which radiation was irradiated without having passed through a subject in a past image capturing, and the control section controls the light illuminating section such that much light is illuminated onto the portion, within the detection region, at which radiation was irradiated without having passed through the subject.

9. A radiographic imaging system comprising:

an imaging panel at which a plurality of sensor portions, that detect radiation or light converted from radiation, are formed at a detection region, and that captures a radiographic image expressed by radiation or light converted from radiation;

a light illuminating section at which a plurality of light-emitting portions, that can individually illuminate light for erasing residual images, are provided per sectional region obtained by dividing an imaging region into a plurality of the sectional regions;

a control section that, in accordance with imaging conditions, controls absence/presence of illumination of, light amount of, and illumination time period of light from the respective light-emitting portions of the light illuminating section; and an acquisition section that acquires a position of an imaging region within the detection region; wherein the control section controls the light illuminating section so as to cause light to be illuminated from the light-emitting portions that correspond to the imaging region acquired by the acquisition section; and wherein the control section causes at least some of the light-emitting portions that correspond to a non-imaging region to emit light at a light amount lower than a light amount of the light-emitting portions that correspond to the imaging region.

* * * * *